(12) United States Patent
Knopp et al.

(10) Patent No.: US 8,449,842 B2
(45) Date of Patent: May 28, 2013

(54) MOLECULAR READER

(75) Inventors: Kevin J. Knopp, Newburyport, MA (US); Daryoosh Vakhshoori, Cambridge, MA (US); Peidong Wang, Carlisle, MA (US); Masud Azimi, Belmont, MA (US); Scott E. Miller, Somerville, MA (US); Jason Goldstein, Salem, NH (US); Stephen McLaughlin, Andover, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 371 days.

(21) Appl. No.: 12/722,211

(22) Filed: Mar. 11, 2010

(65) Prior Publication Data

US 2011/0022324 A1    Jan. 27, 2011

Related U.S. Application Data

(60) Provisional application No. 61/161,642, filed on Mar. 19, 2009.

(51) Int. Cl.
*A61B 10/00* (2006.01)

(52) U.S. Cl.
USPC ............. 422/536; 422/50; 422/500; 422/501; 422/502; 436/180

(58) Field of Classification Search
USPC ............ 422/50, 500–502, 566, 536; 436/180; 204/452
See application file for complete search history.

(56) References Cited

U.S. PATENT DOCUMENTS

| | | | |
|---|---|---|---|
| 4,780,408 A | 10/1988 | Dunbar et al. | |
| 5,981,196 A | 11/1999 | Stavinski et al. | |
| 5,981,298 A | 11/1999 | Chudzik et al. | |
| 6,391,625 B1 | 5/2002 | Park et al. | |
| 6,407,395 B1 | 6/2002 | Perov et al. | |
| 6,420,530 B1 | 7/2002 | Weatherby et al. | |
| 6,494,373 B2 | 12/2002 | Tanaami et al. | |
| 6,512,580 B1 | 1/2003 | Behringer et al. | |
| 6,537,801 B1 | 3/2003 | Ida et al. | |
| 6,620,623 B1 | 9/2003 | Yershov et al. | |
| 6,623,696 B1 | 9/2003 | Kim et al. | |
| 6,635,434 B1 | 10/2003 | Jakobsen et al. | |
| 6,716,620 B2 | 4/2004 | Bashir et al. | |
| 6,787,349 B1 | 9/2004 | Yamamoto et al. | |
| 6,806,954 B2 | 10/2004 | Sandstrom | |

(Continued)

OTHER PUBLICATIONS

Wang, J. et al., "Microfluidic Cell Electroporation Using a Mechanical Valve," Analytical Chemistry 79: 9584-9587 (2007).

*Primary Examiner* — Jyoti Nagpaul
(74) *Attorney, Agent, or Firm* — Gordon Stewart

(57) ABSTRACT

Systems and methods disclosed include: a support apparatus configured to detachably receive a chip; movable pins extendible from a first position to a second position, where, in the first position, the movable pins do not contact a chip positioned on the support apparatus, and in the second position, the movable pins contact electrical terminals of a heating element within a chip positioned on the support apparatus; a radiation source configured to direct radiation to be incident on a chip positioned on the support apparatus; a detector; and an electronic processor, the electronic processor being configured to detect molecules in a sample positioned within the chip, and to determine a temperature of the chip by measuring an electrical resistance between two of the multiple pins connected to the electrical terminals.

34 Claims, 11 Drawing Sheets

U.S. PATENT DOCUMENTS

| | | | |
|---|---|---|---|
| 6,846,650 B2 | 1/2005 | Recipon et al. | |
| 6,856,359 B2 | 2/2005 | Matsushita et al. | |
| 6,867,851 B2 | 3/2005 | Blumenfeld et al. | |
| 6,888,630 B2 | 5/2005 | Tanaami et al. | |
| 6,902,703 B2 | 6/2005 | Marquiss et al. | |
| 6,919,201 B2 | 7/2005 | Tanaami et al. | |
| 6,956,651 B2 | 10/2005 | Lackritz et al. | |
| 6,982,431 B2 | 1/2006 | Modlin et al. | |
| 7,042,565 B2 | 5/2006 | Wang et al. | |
| 7,145,645 B2 | 12/2006 | Blumenfeld et al. | |
| 7,172,897 B2 | 2/2007 | Blackburn et al. | |
| 7,173,701 B2 | 2/2007 | Wang et al. | |
| 7,209,236 B2 | 4/2007 | Tanaami et al. | |
| 7,259,019 B2 | 8/2007 | Pawliszyn et al. | |
| 7,338,763 B2 | 3/2008 | Remacle et al. | |
| 7,435,579 B2 | 10/2008 | Bashir et al. | |
| 7,455,966 B1 | 11/2008 | Schaudies et al. | |
| 7,463,353 B2 | 12/2008 | Yershov | |
| 7,482,585 B2 * | 1/2009 | Sando et al. | 250/288 |
| 7,535,568 B2 | 5/2009 | Sugiyama et al. | |
| 7,602,307 B1 | 10/2009 | Brennan et al. | |
| 7,622,082 B2 | 11/2009 | Tanaami | |
| 7,633,620 B2 | 12/2009 | Nahm et al. | |
| 7,635,563 B2 | 12/2009 | Horvitz et al. | |
| 7,642,085 B2 | 1/2010 | Schultz et al. | |
| 7,666,663 B2 | 2/2010 | Sugiyama et al. | |
| 7,750,316 B2 | 7/2010 | MacCraith et al. | |
| 7,776,195 B2 | 8/2010 | Kureshy et al. | |
| 7,803,541 B2 | 9/2010 | Luo et al. | |
| 7,815,853 B2 | 10/2010 | Nahm et al. | |
| 7,851,251 B2 | 12/2010 | Tseng et al. | |
| 7,902,617 B2 | 3/2011 | Baskaran | |
| 2001/0045358 A1 * | 11/2001 | Kopf-Sill et al. | 204/452 |
| 2009/0032399 A1 | 2/2009 | Jacobson et al. | |

* cited by examiner

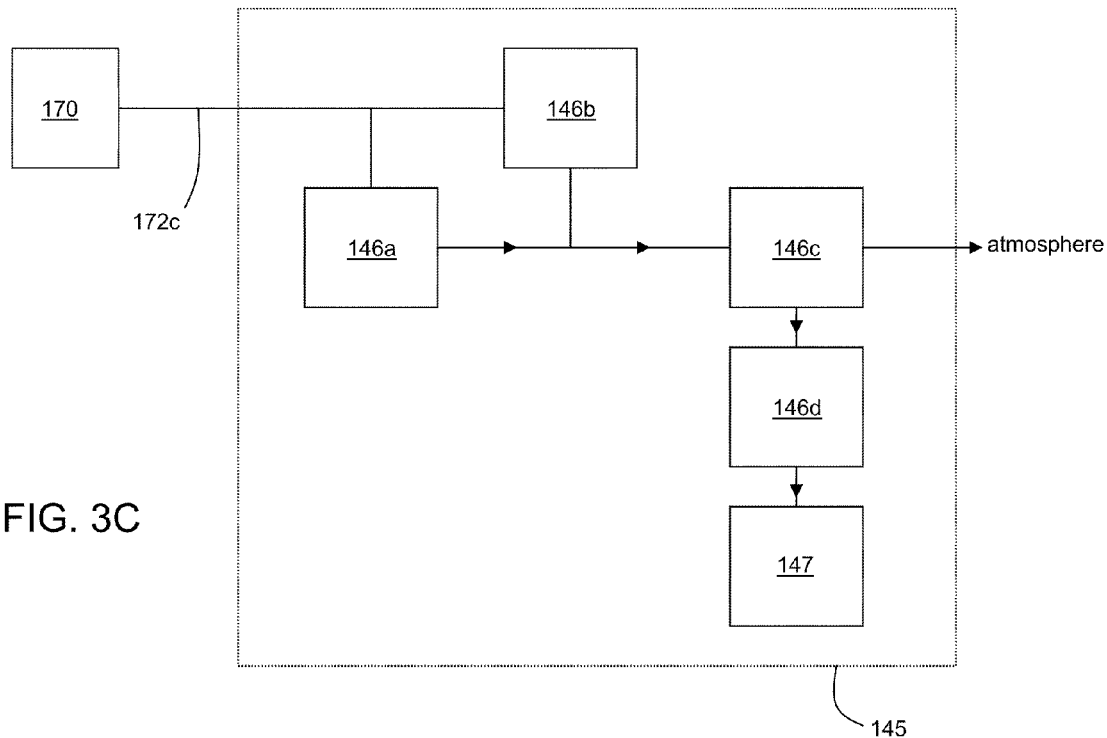
FIG. 3C
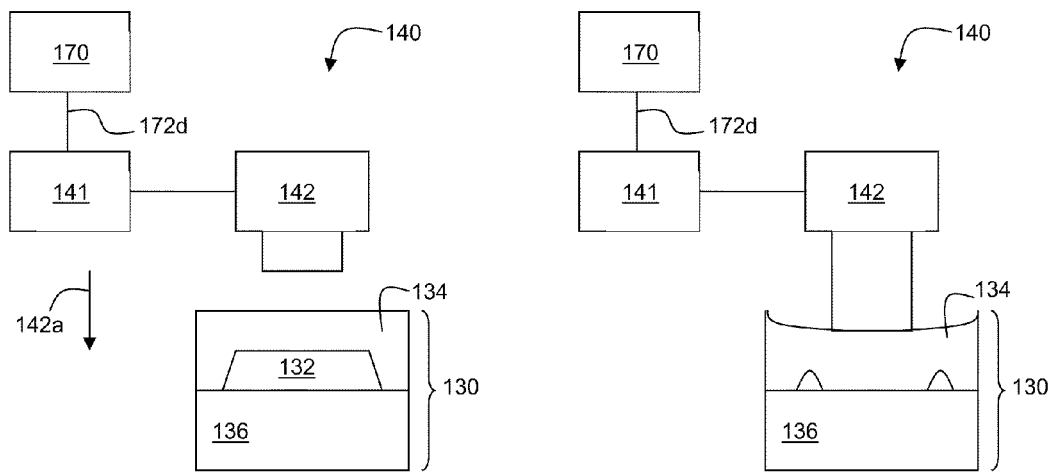
FIG. 4A
FIG. 4B

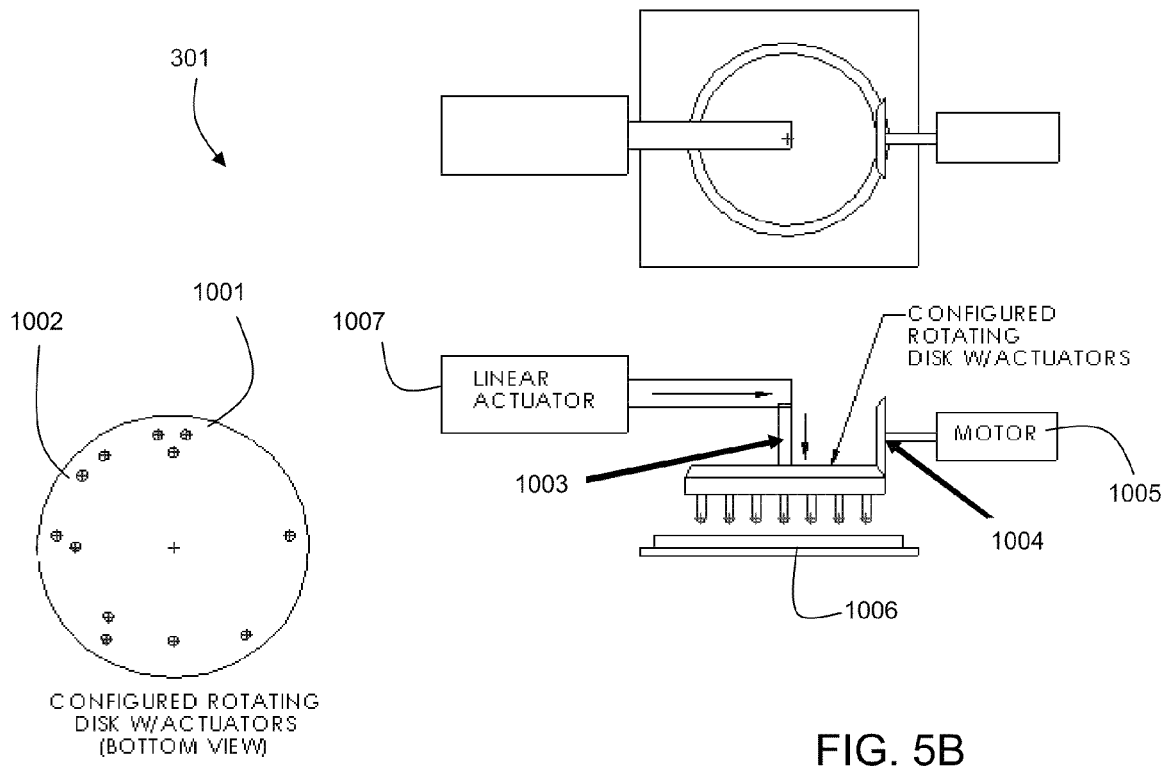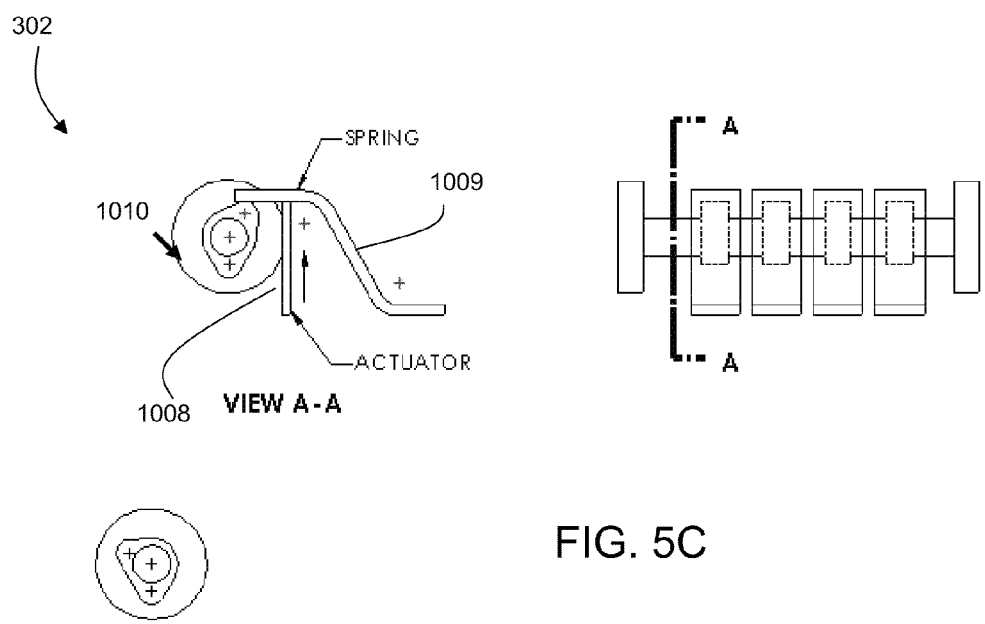
FIG. 5B
FIG. 5C

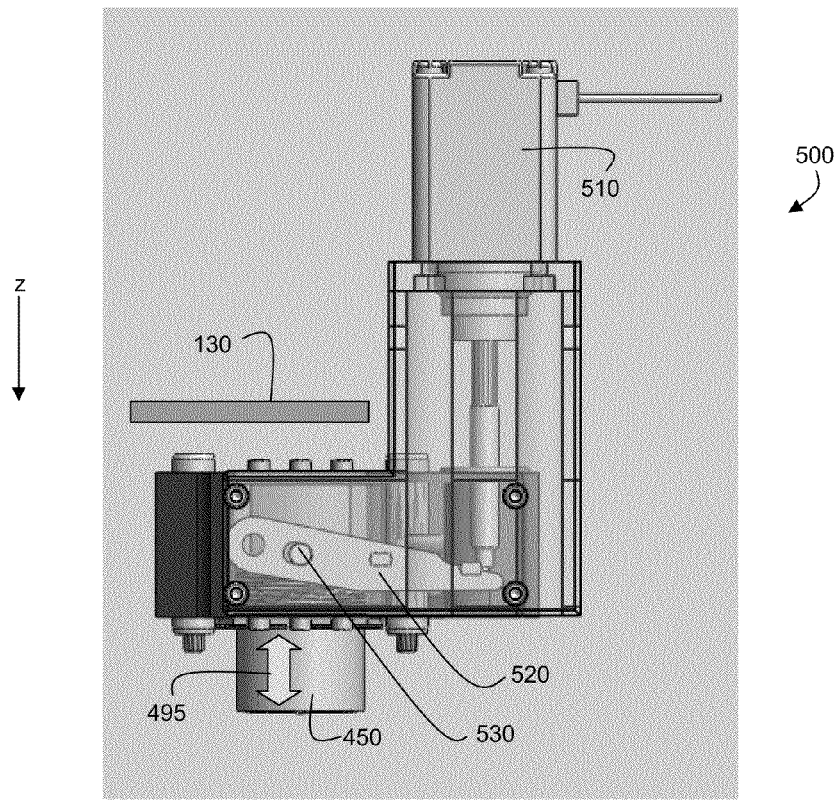
FIG. 8
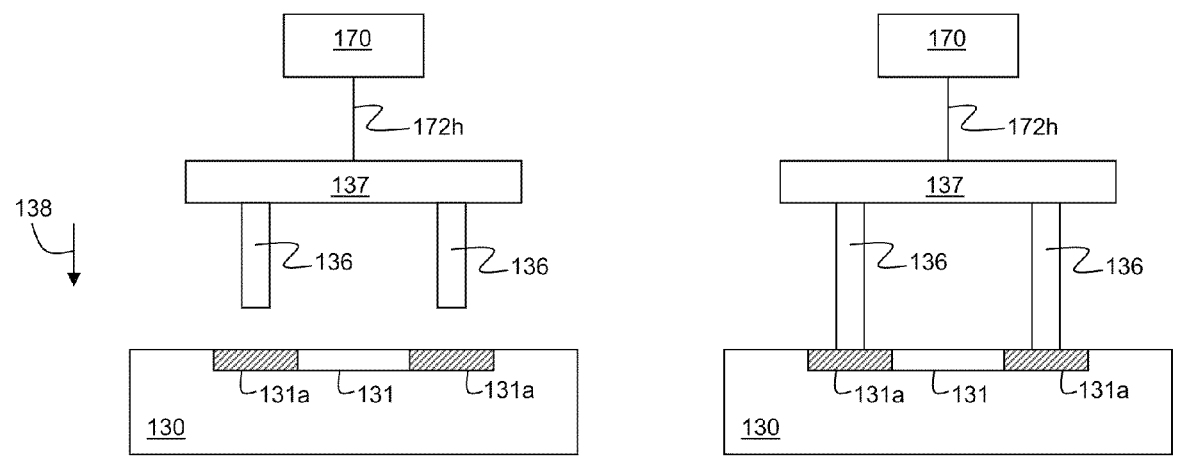
FIG. 9A
FIG. 9B

MOLECULAR READER

CROSS-REFERENCE TO RELATED APPLICATIONS

This application claims priority to U.S. Provisional Application No. 61/161,642, filed on Mar. 19, 2009, the entire contents of which are incorporated herein by reference.

STATEMENT AS TO FEDERALLY SPONSORED RESEARCH

This invention was made with Government support under National Institutes of Health Grant No. 5 U01 DE 017788-03. The Government has certain rights in this invention.

TECHNICAL FIELD

This disclosure relates to detection of chemicals, biological molecules and portions of molecules.

BACKGROUND

Conventional methods for detecting chemicals and biological molecules such as proteins and nucleic acids can be time-consuming and can require expensive laboratory equipment. Detection of such molecules, or fragments thereof, can provide important diagnostic tools for medical testing, security screening, environmental testing, and other applications.

SUMMARY

The ability to detect chemicals and biological molecules with a mechanically robust, portable device, usable with minimal training, can allow analyses to be done outside a traditional laboratory setting. In general, the disclosure discusses a system that allows enables detection of chemicals, biological molecules and portions of molecules. The system can perform optical imaging functions and small-volume fluidic functions, and includes:

In general, in a first aspect, the disclosure features a system that includes: (a) a support apparatus configured to detachably receive a chip; (b) a plurality of movable pins extendible from a first position to a second position, where (i) in the first position, the movable pins do not contact the chip when the chip is positioned on the support apparatus, and (ii) in the second position, the movable pins contact electrical terminals of one or more heating elements within the chip when the chip is positioned on the support apparatus; (c) a compact, high-performance optical system including (i) a radiation source configured to direct radiation to be incident on the chip when the chip is positioned on the support apparatus, and (ii) an imaging detector configured to detect radiation emitted from the chip when the chip is positioned on the support apparatus; and (d) an electronic processor in electrical communication with the plurality of movable pins and the detector, where the electronic processor is configured to detect molecules in a sample positioned within the chip by analyzing the detected radiation, and to determine a temperature of the chip by measuring an electrical resistance between two of the multiple pins connected to the electrical terminals.

In one aspect, an apparatus includes: a compact, portable radiation source/detection system for acquiring a magnified optical image of an object. The compact, portable radiation source/detection system includes: at least one radiation source which projects radiation onto the object; an imaging detector; optics for imaging radiation emitted, reflected, scattered, or otherwise altered by the object in response to the radiation source to the imaging detector to produce the magnified optical image of the object on the detector; and one or more optical filters which prevent >90% of the radiation from the radiation source from being detected by the detector, while allowing the radiation emitted, reflected, scattered, or otherwise altered by the object to be detected by the detector. In some embodiments, the compact, portable radiation source/detection system is rugged. In some embodiments, the optics, the imaging detector and the one or more optical filters are configured to form a magnified fluorescence image of the object on the detector.

In one aspect, systems include a radiation source/detection system for acquiring a magnified optical image of an object; at least one radiation source which projects light onto the object; a lens assembly including at least one optical element for collecting radiation emitted, reflected, scattered, or otherwise altered by the object; a lens assembly including at least one optical element for conveying the image or altered radiation to the detector; a detector for collecting light emitted, reflected, scattered, or otherwise altered by the object; one or more optical filters which prevent >90% of radiation from at least one radiation source from being detected by the detector, while allowing radiation emitted, reflected, scattered, or otherwise altered by the object to be detected.

Embodiments of the systems and apparatus can include one or more of the following features.

The system can include a miniaturized optical subsystem for high-resolution 2-D imaging. The optical subsystem can include one or more radiation sources. Each radiation source provides light to an object or area of interest, allowing the object to be imaged.

In some embodiments, systems also include a support apparatus configured to detachably receive a microfluidic chip. In some cases, systems also include an electronic processor in electrical communication with the radiation sources and the detector, wherein the electronic processor is configured to process the detected radiation or image. Systems can also include a movable lens system electrically coupled to the electronic processor. During use, the electronic processor can be configured to adjust a depth of focus of the detected radiation by translating at least one lens of the movable lens system. The movable lens system can include a movable actuator, a movable objective lens, and a pivoting member connected to the actuator and to the objective lens, and wherein during use the electronic processor adjusts the depth of focus by adjusting an extension of the actuator.

In some cases, the detector is configured to acquire an image of the chip when the chip is received by the support apparatus, and wherein the electronic processor is configured to determine the position of the chip based on the image. The electronic processor can be configured to determine whether the chip is positioned correctly based on the image.

In some embodiments, the detected radiation comprises fluorescence emission from a sample positioned within the chip.

In some embodiments, the electronic processor is configured to detect two or more different types of molecules in a sample positioned within the chip by analyzing the detected radiation at one central wavelength. In some cases, the electronic processor is configured to detect at least one of molecules comprising amino acids and molecules comprising nucleic acids in a sample positioned within the chip.

The optical subsystem can further include a detector which can be configured to acquire an image of the object or an area of interest, and the electronic processor can be configured to determine the position of the chip based on the image. The detector occupies minimal space in the system and is capable of detecting low levels of light with low noise while consuming minimal electrical power. The electronic processor can be configured to determine whether the chip is positioned correctly based on the image.

The optical subsystem can further include wavelength filters, which prevent unadulterated radiation from at least one of the radiation sources from being detected by the detector, while allowing radiation emitted, scattered, or otherwise altered by the object to be detected.

The detected radiation can include fluorescence emission from a sample positioned within a microfluidic chip. The detected radiation can also include radiation scattered or reflected from a sample positioned within the chip.

The subsystem can include a movable lens system electrically coupled to the electronic processor. During use, the electronic processor can be configured to adjust the position of focus of the detected radiation by translating at least one lens of the movable lens system. The movable lens system can include a movable actuator, a movable objective lens, and a pivoting member connected to the actuator and to the objective lens, and during use, the electronic processor can adjust the depth of focus by adjusting an extension of the actuator.

The electronic processor can be configured to cause at least some of the plurality of movable pins to extend from the first position to the second position when the chip is received by the support apparatus. The electronic processor can be configured to interact with one or more thermistors integrated into the chip to control the temperature of the chip by applying an electrical potential differences between the electrical terminals of the thermistors.

The system can include a movable vacuum source extendible from a first vacuum position not in contact with the chip to a second vacuum position in contact with the chip when the chip is positioned on the support apparatus. The electronic processor can be configured to extend the vacuum source from the first vacuum position to the second vacuum position to form a fluid connection with a channel positioned in the chip.

The system can include at least one extendible member electrically connected to the electronic processor and positioned so that when the chip is received by the support apparatus, the at least one extendible member contacts the chip and extends to deform a wall of a channel formed within the chip. The at least one extendible member can include a motorized actuator coupled to the electronic processor. The motorized actuator can include a rotatable shaft coupled to a motor, where the rotatable shaft extends in a direction parallel to a central axis of the shaft. Alternatively, or in addition, the motorized actuator can include a shaft coupled to a rotatable disc that includes at least one pin, where the at least one pin deforms the wall of the channel. Alternatively, or in addition, the motorized actuator can include at least one pin coupled to a spring, and the actuator can include a rotating camshaft that controls an extension of the at least one pin. The at least one extendible member can include four extendible members.

The electronic processor can control movement of the at least one extendible member between a first position where the at least one extendible member applies a first pressure to the channel wall, and a second position where the at least one extendible member applies a second pressure different from the first pressure to the channel wall. The electronic processor can control an open cross-sectional area of the channel by controlling the extension of the at least one extendible member.

The system can include a housing that encloses the support apparatus, the plurality of movable pins, the radiation source, the detector, and the electronic processor, the housing having an opening through which the chip can be received by the support apparatus, and a closing member adjustable between an open position wherein the opening is at least partially unobstructed by the closing member and a closed position wherein the closing member seals the opening. The closing member can be mechanically coupled to at least some of the plurality of movable pins so that when the closing member is moved from the open position to the closed position, the at least some of the plurality of movable pins are moved from the first position to the second position.

The electronic processor can be configured to detect two or more different types of molecules in a sample positioned within the chip by analyzing the detected radiation at one central wavelength. The electronic processor can be configured to detect at least one of molecules that include amino acids and molecules that include nucleic acids in a sample positioned within the chip. The electronic processor can be configured to detect both molecules that include amino acids and molecules that include nucleic acids in a sample positioned within the chip.

The system can include a communications interface, where the electronic processor is configured to transmit data to, and receive data from, one or more external devices through the communications interface. The communications interface can include a wireless transmitter and receiver electrically coupled to the electronic processor and configured to transmit and receive electronic signals.

The heating element can include a thermistor. The electrical terminals can include a conductive epoxy material.

Embodiments of the system can also include any of the other features disclosed herein, as appropriate.

In another aspect, the disclosure features a system that includes: (a) a support apparatus configured to detachably receive a chip; (b) at least one extendible member positioned so that when the chip is received by the support apparatus, the at least one extendible member contacts the chip and extends to deform a wall of a channel formed within the chip; (c) a compact, high-performance optical system including (i) a radiation source configured to direct radiation to be incident on the chip when the chip is positioned on the support apparatus, and (ii) an imaging detector configured to detect radiation emitted from the chip when the chip is positioned on the support apparatus; and (d) an electronic processor in electrical communication with the at least one extendible member and the detector. The electronic processor is configured to detect molecules in a sample positioned within the chip by analyzing the detected radiation. The electronic processor is configured to regulate a flow of fluid through the channel by controlling an extension of the at least one extendible member.

In another aspect, the disclosure features a system that includes: (a) a support apparatus configured to detachably receive a chip; (b) at least one extendible member positioned so that when the chip is received by the support apparatus, the at least one extendible member contacts the chip and extends to deform a wall of a channel formed within the chip; (c) a radiation source configured to direct radiation to be incident on the chip when the chip is positioned on the support apparatus; (d) a detector configured to detect radiation emitted from the chip when the chip is positioned on the support apparatus; and (e) an electronic processor in electrical communication with the at least one extendible member and the detector. The electronic processor is configured to detect molecules in a sample positioned within the chip by analyzing the detected radiation. The electronic processor is configured to regulate a flow of fluid through the channel by controlling an extension of the at least one extendible member.

Embodiments of the system can include one or more of the following features.

The system can include a plurality of movable pins extendible from a first position to a second position, where (i) in the first position, the movable pins do not contact the chip when the chip is positioned on the support apparatus, and (ii) in the second position, the movable pins physically interact with the chip. One possible interaction is for the pins to contact electrical terminals of a heating element within the chip when the chip is positioned on the support apparatus, and where the electronic processor is in electrical communication with the plurality of movable pins. The electronic processor can be configured to cause at least some of the plurality of movable pins to extend from the first position to the second position when the chip is received by the support apparatus. The electronic processor can be configured to control a temperature of the chip by applying an electrical potential difference between the electrical terminals.

The system can include a movable vacuum source extendible from a first vacuum position not in contact with the chip to a second vacuum position in contact with the chip when the chip is positioned on the support apparatus. The electronic processor can be configured to extend the vacuum source from the first vacuum position to the second vacuum position to form a fluid connection with a vacuum channel positioned in the chip.

The at least one extendible member can include a motorized actuator coupled to the electronic processor. The motorized actuator can include a rotatable shaft coupled to a motor, where the rotatable shaft extends in a direction parallel to a central axis of the shaft. Alternatively, or in addition, the motorized actuator can include a shaft coupled to a rotatable disc that includes at least one pin, where the at least one pin deforms the wall of the channel. Alternatively, or in addition, the motorized actuator can include at least one pin coupled to a spring, and a rotating camshaft that controls an extension of the at least one pin.

The electronic processor can control movement of the at least one extendible member between a first position where the at least one extendible member applies a first pressure to the channel wall, and a second position where the at least one extendible member applies a second pressure different from the first pressure to the channel wall.

The system can include a housing that encloses the support apparatus, the at least one extendible member, the radiation source, the detector, and the electronic processor, the housing having an opening through which the chip can be received by the support apparatus, and a closing member adjustable between an open position where the opening is at least partially unobstructed by the closing member and a closed position wherein the closing member seals the opening.

The system can include a housing that encloses the support apparatus, the plurality of movable pins, the at least one extendible member, the radiation source, the detector, and the electronic processor, the housing having an opening through which the chip can be received by the support apparatus, and a closing member adjustable between an open position where the opening is at least partially unobstructed by the closing member and a closed position wherein the closing member seals the opening, and where the closing member is mechanically coupled to at least some of the plurality of movable pins so that when the closing member is moved from the open position to the closed position, the at least some of the plurality of movable pins are moved from the first position to the second position.

The heating element can include a thermistor. The electrical terminals can include a conductive epoxy material.

Embodiments of the system can also include any of the other features disclosed herein, as appropriate.

In a further aspect, the disclosure features a method that includes: (a) positioning a chip on a support stage configured to detachably receive the chip; (b) extending a plurality of movable pins from a first position not in contact with the chip to a second position where the movable pins contact electrical terminals of a heating element within the chip; (c) directing illumination radiation to be incident on the chip; (d) measuring radiation emitted from the chip; and (e) detecting molecules in a sample positioned within the chip based on the measured radiation.

Embodiments of the method can include one or more of the following features.

The method can include measuring a temperature at one or more locations on the chip by applying an electrical potential difference between the electrical terminals of one or more thermistors integrated on the chip. The method can include controlling a temperature at one or more locations on the chip by applying an electrical potential difference between the electrical terminals of the same thermistors integrated on the chip.

The method can include positioning an extendible member so that the member contacts a wall of a channel formed in the chip. The method can include regulating a flow of fluid through the channel by extending the extendible member to control a cross-sectional shape of the channel. The method can include positioning a vacuum source into fluid communication with a vacuum channel formed in the chip. The method can include, prior to extending the plurality of movable pins, measuring an image of the chip on the support stage and determining a position of the chip relative to the stage based on the image.

The molecules in the sample can be detected based on a measurement of emitted radiation. Detecting molecules in the sample can include detecting both molecules that include amino acids and molecules that include nucleic acids in the sample.

Embodiments of the method can also include any of the other features or method steps disclosed herein, as appropriate.

In another aspect, the disclosure features a method that includes: (a) positioning a chip on a support stage configured to detachably receive the chip; (b) positioning an extendible member so that the member contacts a wall of a channel formed in the chip; (c) regulating a flow of fluid through the channel by extending the extendible member to control a cross-sectional shape of the channel; (d) directing illumination radiation to be incident on the chip; (e) measuring radiation emitted from the chip; and (f) detecting molecules in a sample positioned within the chip based on the measured radiation.

Embodiments of the method can include one or more of the following features.

The method can include extending a plurality of movable pins from a first position not in contact with the chip to a second position wherein the movable pins contact electrical terminals of a heating element within the chip;

The method can include measuring a temperature of the chip by applying an electrical potential difference at one or more locations on the chip by applying an electrical potential difference between the electrical terminals of one or more thermistors integrated on the chip. The method can include controlling a temperature at one or more locations on the chip by applying an electrical potential difference between the electrical terminals of the same thermistors integrated on the chip. The method can include positioning a vacuum source into fluid communication with a vacuum channel formed in the chip. The method can include, prior to positioning the extendible member, measuring an image of the chip on the support stage and determining a position of the chip relative to the stage based on the image.

The molecules in the sample can be detected based on a measurement of emitted radiation at one central wavelength. Detecting molecules in the sample includes detecting both molecules that include amino acids and molecules that include nucleic acids in the sample.

Embodiments of the method can also include any of the other features or method steps disclosed herein, as appropriate.

In a further aspect, the disclosure features a microfluidic chip that includes a plurality of enclosed channels configured to allow fluid to flow through at least some of the channels, and a heating element that includes electrical terminals that extend to an exterior surface of the chip, where the chip is configured so that when it is electrically connected to an electronic processor through the electrical terminals, the electronic processor can determine the temperature at one or more of the chip by measuring a resistance of the heating element, and the electronic processor can control the temperature of the chip by applying an electrical potential difference between the electrical terminals.

In a further aspect, microfluidic chips, include: a plurality of enclosed channels configured to allow fluid to flow through at least some of the channels; an array of capture sites configured to chemically bind analyte molecules in a sample, wherein the array of capture sites is in hydraulic communication with the fluid channels; and a thermistor with electrical terminals that extend to an exterior surface of the chip, the thermistor positioned to measure and control a temperature of the array of capture sites.

Embodiments of the chip can include one or more of the following features.

The chip can include a plurality of fluid channels in hydraulic communication with a chamber configured to contain a sample. The chip can include a substrate layer, a channel layer, and a top layer, the channel layer being formed of a material that is more deformable than a material of the top layer, where the plurality of fluid channels are formed in the channel layer. At least some of the fluid channels can include channel walls that deform reversibly when a force is applied to the walls. The top layer can include a plurality of apertures positioned to expose portions of walls of at least some of the fluid channels formed in the channel layer. The substrate layer can be formed of glass, the channel layer can be formed of a polymer material, and the top layer can be formed of plastic.

The chip can include a vacuum channel in hydraulic communication with at least some of the fluid channels, and configured to form a fluid connection with an external vacuum source or pump source. The chip can include a plurality of reservoirs in hydraulic communication with the fluid channels, where at least one of the plurality of reservoirs is configured to contain a buffer solution, at least one of the plurality of reservoirs is configured to contain a tagging agent, and at least one of the reservoirs is configured to receive waste fluids.

The electrical terminals can include a conductive epoxy material. The heating element can include a thermistor.

The chip can be configured for use in a feedback circuit or algorithm, where the measured temperature of the chip is used to determine the electrical potential difference that is applied between the electrical terminals to control the temperature of the chip.

The chip can include an array of capture sites configured to chemically bind analyte molecules in a sample, where the array of capture sites is in hydraulic communication with the fluid channels. The array of capture sites can be configured to chemically bind both molecules that include nucleic acids, and molecules that include amino acids.

The heating element can be positioned to measure and control a portion of the chip where the array of capture sites are located.

Embodiments of the chip can also include any of the other features disclosed herein, as appropriate.

In a further aspect, a method includes: determining a temperature of a portion of a microfluidic chip, the portion containing an array of capture sites configured to chemically bind specific target molecules, by measuring an electrical resistance of a heating element disposed on the microfluidic chip; and controlling the temperature of the portion of the microfluidic chip containing the array of capture sites by applying an electrical potential difference across the heating element.

Embodiments of the method can include one or more of the following features.

The method can include inserting the microfluidic chip into an analysis device. The method can also include a sample from a reservoir on the microfluidic chip to the array of capture sites through a plurality of fluid channels. The method can also include applying a force to exterior surfaces of the microfluidic chip to reversibly deform walls of at least some of the fluid channels.

The heating element can include a thermistor.

The method can include using a feedback circuit or algorithm wherein the measured temperature of the chip is used to determine the electrical potential difference that is applied between the electrical terminals to control the temperature of the chip.

The details of one or more embodiments are set forth in the accompanying drawings and the description below. Other features and advantages will be apparent from the description, drawings, and claims. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF DRAWINGS

FIG. 3C is a schematic diagram showing components of a vacuum control module.

FIGS. 4A and 4B are schematic diagrams of an actuator control module in a retracted and an extended position, respectively.

FIG. 5B is a schematic diagram of a rotating-disk actuator.

FIG. 5C is a schematic diagram of a cam and leaf-spring actuator.

FIG. 8 is a schematic diagram showing an autofocusing assembly of a molecular reader.

FIGS. 9A and 9B are schematic diagrams showing a thermal control module in a retracted and an extended position, respectively.

Like reference symbols in the various drawings indicate like elements.

DETAILED DESCRIPTION

Devices for detecting (e.g., reading) molecules such as proteins and nucleic acids are typically relatively sophisticated, laboratory-based devices. Samples that include analytes of interest are brought to the laboratory, prepared for analysis, and introduced into a detection device. Over a period that can range between a few hours and several days, depending upon the nature of the analysis, the sample is analyzed for the presence of various biological molecules. Many such molecules function as genetic markers and/or identifiers, as bio-markers for disease agents, and/or as indicators of therapeutic efficacy of medicinal treatments.

The molecular readers disclosed herein are portable, mechanically robust, relatively inexpensive, and permit detection and/or analysis of different types of biological molecules (e.g., amino acid-based molecules such as proteins and protein fragments, nucleic acid-based molecules such as DNA, RNA, and fragments). The readers are usable by minimally-trained personnel. The readers permit analysis of multiple different types of molecules and/or samples on a single sandwich-type chip by performing functions related to imaging, fluidic control, and thermal control. Analysis times generally range from a few hours to less than an hour, depending upon such factors as the amount of analyte in a sample and the marker used to tag the analyte.

I. System Overview

Figure 1:
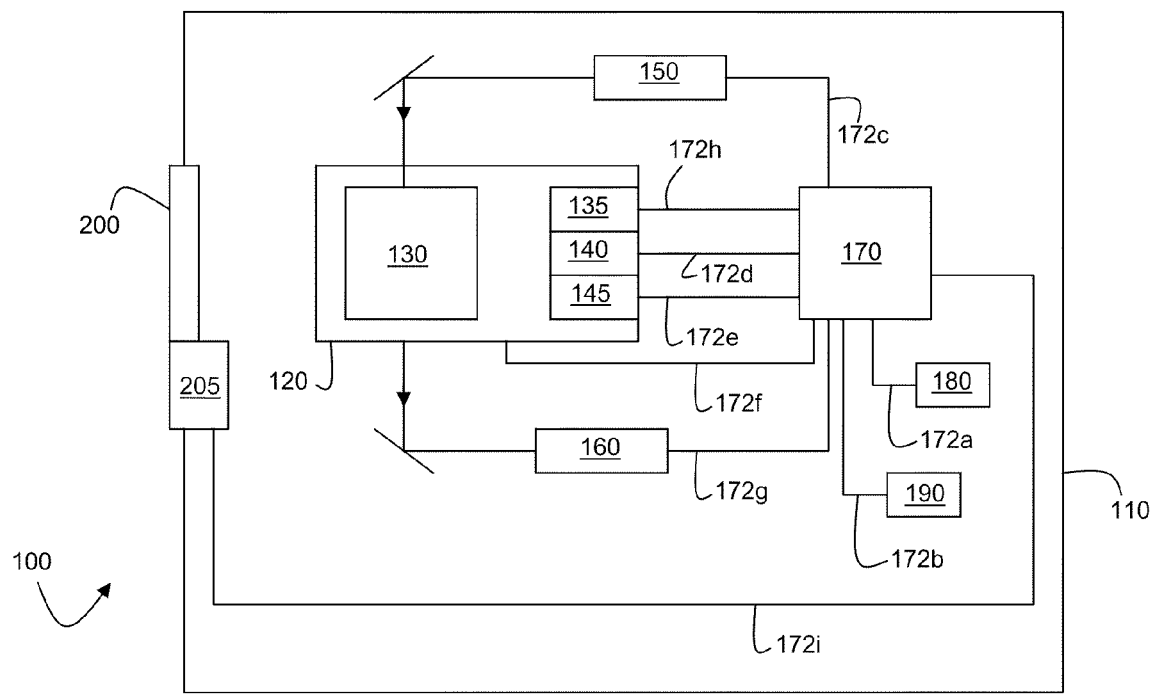
FIG. 1 is a schematic diagram of an embodiment of a molecular reader.

FIG. 1 shows a schematic diagram of a molecular reader 100. Reader 100 includes a housing 110, a stage 120 that supports a chip 130, a thermal control module 135, an actuator control module 140, a vacuum control module 145, a radiation source 150, a radiation detector 160, an electronic processor 170, a communications interface 180, and a display interface 190. Electronic processor 170 is connected to stage 120, thermal control module 135, actuator control module 140, vacuum control module 145, radiation source 150, radiation detector 160, communications interface 180, and display interface 190 via control lines 172a-h.

In general, during operation, chip 130 is introduced into reader 100 via access port 200 in housing 110. Access port 200 can include an open slot, or can include a door which, when closed, separates the interior of the reader 100 from the environment. The door can be closed manually, or the door can be connected to a motorized actuator 205 that closes the door in response to a signal from electronic processor 170 via control line 172i. Chip 130, which will be discussed in greater detail subsequently, can hold one or more samples of interest. Stage 120 is configured to receive chip 130 when it is inserted into reader 100, and to secure chip 130 once it is inside the reader. Chip 130 is either pre-loaded with one or more samples, or samples can be introduced into chip 130 once it is secured in reader 100.

Samples are present in chip 130 in liquid form (e.g., as neat liquids, or as solutions). Electronic processor 170 directs actuator control module 140 and vacuum control module 145 to cause a portion of the sample (or a portion of one of the on-board samples) to flow from a reservoir region of the chip to an analysis region of the chip. Typically, the analysis region of the chip includes multiple, spatially-separated sites that include binding "capture" agents that selectively bind the analytes of interest in the sample. For example, if the analytes of interest in the sample are proteins or protein fragments, chip 130 includes one or more types of antibodies that selectively bind the proteins or protein fragments. If the analytes of interest are nucleic acid molecules (DNA, RNA) or portions thereof, chip 130 includes one or more types of complementary nucleic acids that selectively bind the nucleic acids of interest.

Once sufficient time has passed for the analytes of interest to be bound to the analysis region of the chip, electronic processor 170 further directs actuator control module 140 and vacuum control module 145 to introduce a tagging agent into the analysis region of the chip. The tagging agent can include, for example, a fluorescent marker that selectively binds to the bound analyte in the analysis region. After the excess tagging agent is washed away, the bound analyte can be detected and/or analyzed optically.

A variety of different tagging agents can be used to tag analytes of interest. Common tagging agents include, for example, antibody-based or complementary nucleic acid-based agents that include one or more fluorophores which fluoresce following excitation with suitably-chosen radiation. Other agents which can be used include selective-binding agents that absorb, reflect, phosphoresce, or otherwise emit radiation or alter incident radiation in a manner that can be detected. In some embodiments, multi-component tagging agents can be used. For example, rather than attaching the fluorophore directly to a secondary antibody, the fluorophore can be attached to a streptavidin protein, while the secondary antibody is attached to a biotin molecule. The fluorophore is then linked to the analyte in a two-step process.

Electronic processor 170 then causes radiation source 150 to direct radiation towards the analysis region of the chip, where the analyte of interest is bound and tagged. As an example, the incident radiation can be absorbed by fluorophores present in the tagging agent used to tag the analyte of interest. Radiation detector 160 detects radiation that is emitted from the analysis region of the chip. For example, if the tagging agent includes fluorophores, the emitted radiation can correspond to fluorescence radiation emitted by the fluorophores. Alternatively, for example, the detected radiation can correspond to phosphorescence radiation from the tagging agent, to partially-absorbed incident radiation, and/or to other types of radiation. The detected radiation is then analyzed by electronic processor 170 and used to identify the analyte(s).

II. Molecular Reader Components

1. Support Stage

Figure 2A:
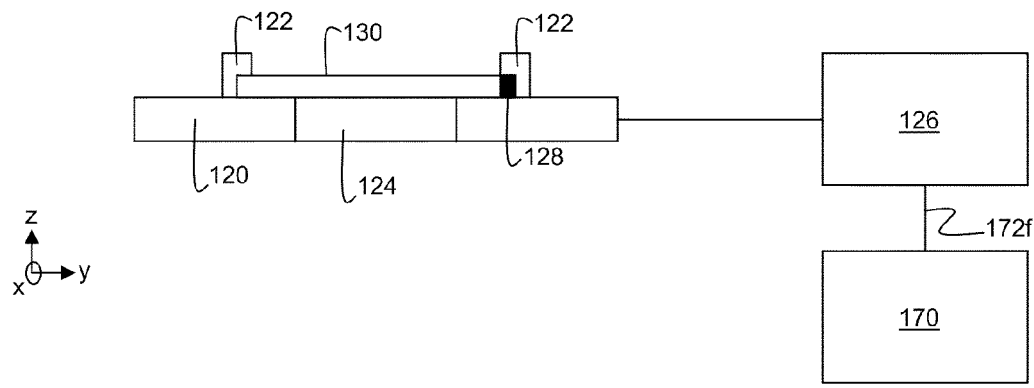
FIG. 2A is a schematic diagram of an embodiment of a support stage.

FIG. 2A shows a schematic diagram of support stage 120. Support stage 120 is configured to support chip 130 when the chip is inserted into reader 100. A control module 126 is electrically connected to support stage 120 and to electronic processor 170. Control module 126 can receive instructions from electronic processor 170 and adjust support stage 120 based on the instructions. For example, in some embodiments, a sensor 128 is positioned on support stage 120. When chip 130 is inserted into reader 100 and onto support stage 120, sensor 128 reports the presence of chip 130 to electronic processor 170 (either directly, or through control module 126). Electronic processor 170 then directs control module 126 to activate movable clamps 122, which lock chip 130 in place on support stage 120. In certain embodiments, movable clamps 122 can be activated and/or released manually, for example, by a system operator who selects a control on display interface 190. In some embodiments, support stage 120 immobilizes chip 130 using reduced pressure (e.g., support stage 120 functions as a vacuum table). In certain embodiments, the presence and correct positioning of chip 130 is verified by acquisition of an optical image of chip 130 using light source 150 and light detector 160. Mathematical analysis of the acquired image (e.g., performed by electronic processor 170) is used to verify that chip 130 is present and positioned correctly on support stage 120.

In general, control module 126 can translate stage 120 along any of the x, y, and z axes, as shown in FIG. 2A, to permit alignment of chip 130 with one or more optical elements of reader 100, for example. By translating stage 120, molecular reader 100 can compensate for small variances in chip dimensions; imaging effects that can arise from such variances (e.g., imaging aberrations) can be reduced and/or eliminated by adjusting the alignment of chip 130 with respect to the optical elements of molecular reader 100.

In certain embodiments, stage 120 can be configured to accept chips having a particular size and shape, where variances in the size and/or shape of the accepted chips can be small enough that no alignment step occurs prior to measuring emitted radiation from the chips. Stage 120 can include a non-adjustable support surface configured to accept chips 130, for example, and to maintain the accepted chips in a suitable position relative to one or more optical components of molecular reader 100, so that fluorescence measurements, for example, can be performed.

In some embodiments, stage 120 can also be rotated about any one or more of the x, y, and z axes to provide further positioning flexibility. The orientation and position of stage 120 is controlled by electronic processor 170 through control module 126. In addition to performing instructions relayed by electronic processor 170, control module 126 reports information to electronic processor 170 via control line 172$f$ (e.g., the position and orientation of stage 120).

In some embodiments, stage 120 can include an aperture 124 as shown in FIG. 2A. Aperture 124 permits through-plane detection of emitted radiation from chip 130. For example, in embodiments of reader 100 where source 150 is positioned on one side of chip 130 and detector 160 is positioned on the opposite side of chip 130, aperture 124 permits emitted radiation to escape from chip 130 and be detected by detector 160. In certain embodiments, source 150 and detector 160 are positioned on the same side of chip 130 (e.g., in an epi-fluorescence illumination configuration). In these embodiments, stage 120 may not include aperture 124 because through-plane emitted light is not measured.

Figure 2B:
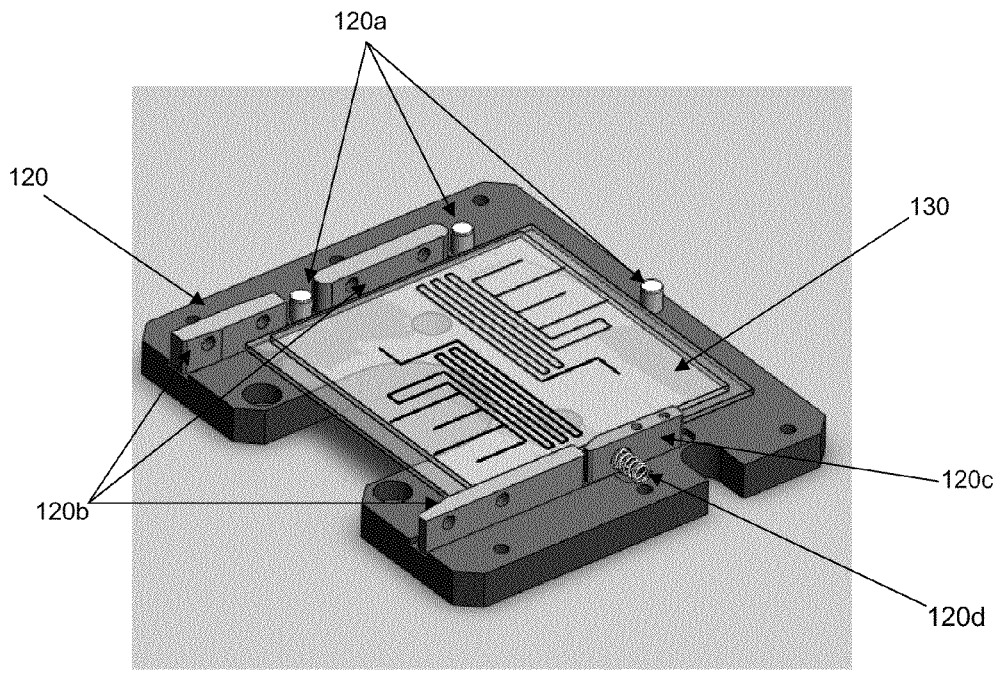
FIG. 2B is a perspective view of an embodiment of a support stage.

A perspective view of an embodiment of stage 120 is shown in FIG. 2B. Stage 120 permits simple, manual placement of microfluidic chips with high positional accuracy. Three cylindrical index pins 120$a$, three static guides for chip insertion 120$b$, and a mobile guide 120$c$ mounted to a small spring 120$d$ assist in reproducibly positioning the chips. A chip 130 is inserted by hand until it touches the back indexing pin 120$a$. Spring 120$d$ applies a force perpendicular to the direction of insertion, holding the chip in place while allowing it to be easily inserted and removed.

In certain embodiments, stage 120 can include a removable cartridge. To load chip 130, the chip is first loaded into the cartridge, and then the cartridge is inserted into reader 100. The use of a cartridge may help to prevent breakage of chips during handling, and may facilitate insertion and removal of chips (for example, the cartridge can include a handle or other shaped element that facilitates grasping by an operator's hand). In some embodiments, the cartridge can contain chemical reagents or other fluids needed for the analysis. In embodiments where through-plane detection is implemented, the cartridge can include an aperture and/or a transparent lower surface to permit emitted light to escape from chip 130 and be detected by detector 160.

2. Fluid Propulsion Control System

Figure 3A:
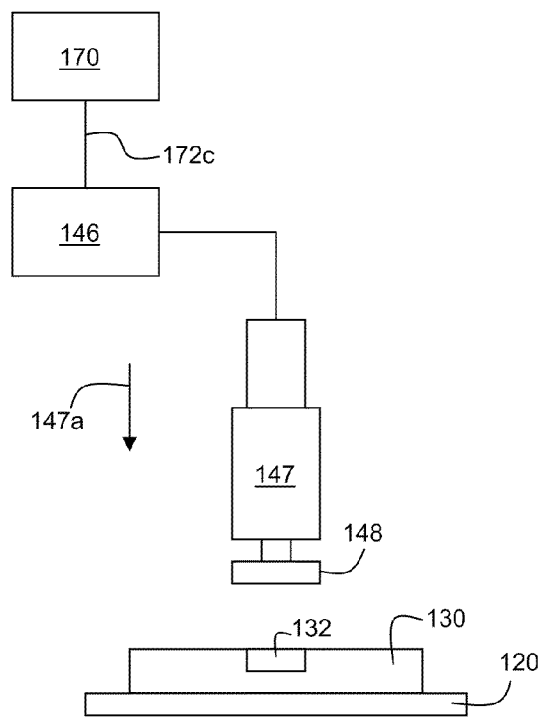
FIGS. 3A and 3B are schematic diagrams of a vacuum control module in a retracted and an extended position, respectively.

Chip 130 includes a plurality of fluid channels formed in a deformable material such as a polymer. Fluids, including the sample of interest, are conveyed on chip 130 from one region to another through the fluid channels. Fluid flow through the channels is achieved by introducing a pressure differential in chip 130 using vacuum control module 145. FIG. 3A shows a schematic diagram of vacuum control module 145, and FIG. 3C shows a schematic diagram that includes various interconnected components of module 145. Vacuum control module 145 includes a vacuum source (146$a$), a vacuum gauge (146$b$), and a vacuum adjustment control (146$c$), a filter (146$d$), and a vacuum nozzle 147. Vacuum source 146$a$ and vacuum gauge 146$b$ are connected to electronic processor 170 via control lines 172$c$. Vacuum source 146$a$ receives instructions from electronic processor 170, and vacuum gauge 146$b$ reports the level of vacuum applied to the chip 130 to electronic processor 170.

Vacuum source 146$a$ can include any one or more of various devices that can produce a vacuum, including a diaphragm pump, a rotary vane pump, a syringe pump, a manual plunger, a Venturi pump, and the like. Vacuum gauge 146$b$ can include a mechanical gauge, a diaphragm gauge, a piezoresistive gauge, and other similar pressure measurement devices. Vacuum adjustment control 146$c$ includes an opening to the atmosphere, and can be a manual needle valve or an active valve that can be controlled by electronic processor 170. Vacuum filter 146$d$ prevents fluids and biological contaminants from being pulled into the vacuum system. Filter 146$d$ typically has a pore size of about 0.2 µm (although filters with many different pore sizes can be used), which blocks the passage of microorganisms including viruses. Typically, the portion of the assembly that includes vacuum filter 146$d$ and nozzle 147 can be easily replaced in the event of a contamination.

As shown in FIG. 3A, nozzle 147 is typically in a disengaged position when chip 130 is inserted into reader 100. When chip 130 is inserted, electronic processor 170 is notified (e.g., via sensor 128, for example, or manually via an instruction from a system operator entered through display interface 190. Electronic processor 170 instructs controller 146 to move nozzle 147 into fluid connection with channel 132 formed in chip 130, by translating nozzle 147 in the direction of arrow 147a.

In certain embodiments, when chip 130 is inserted, a system operator manually closes a door covering access port 200. The door is mechanically linked to a mechanism that lowers nozzle 147 onto chip 130. That is, the action of closing the door initiates translation of nozzle 147.

Figure 3B:
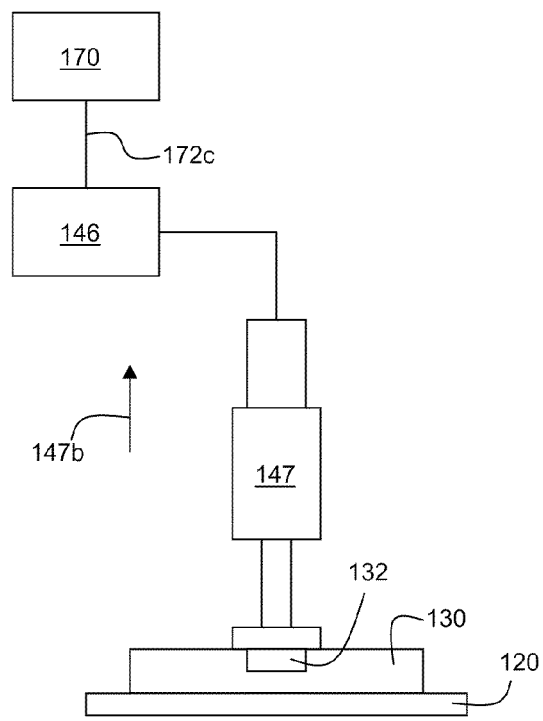

FIG. 3B shows nozzle 147 in fluid connection with channel 132. O-ring 148 is positioned on the end of nozzle 147, and can provide an air- and liquid-tight connection between nozzle 147 and channel 132. O-ring 148 also provides a force-feedback mechanism that indicates to controller 146 that a connection has been established. During operation, controller 146 applies an electrical current to drive a motor which translates nozzle 147 toward chip 130. As o-ring 148 makes contact with chip 130 and is compressed between nozzle 147 and chip 130, the amount of current that controller 146 must supply to the driving motor to continue translating nozzle 147 downward increases, due to the increasing elastic force of o-ring 148 that opposes the motion of nozzle 147. When the current supplied by controller 146 reaches a threshold value, further translation of nozzle 147 is halted.

Once nozzle 147 has been translated to form a suitable fluid connection with channel 132, electronic processor 170 activates vacuum source 146a, which evacuates nozzle 147 and channel 132 in communication with nozzle 147. The pressure differential introduced between the opening of channel 132 (where nozzle 147 is connected) and in other parts of both channel 132 and other channels connected to channel 132 can cause one or more fluids to propagate through the channels.

In the foregoing discussion, nozzle 147 is connected to o-ring 148 that seals the connection with channel 132. In general, a variety of other nozzles can be used in addition to, or in the alternative to, the nozzle shown in FIG. 3A. For example, in some embodiments, nozzle 147 can be implemented in the form of a bellows suction cup. The flexible bellows is compressed when nozzle 147 is lowered, making a seal with chip 130.

Disengagement of nozzle 147 from channel 132 can be initiated either automatically (e.g., in the event of an error condition, or following completion of sample analysis) or in response to an instruction from a system operator (e.g., an instruction entered via display interface 190). Electronic processor 170, through controller 146, halts the vacuum pump, causing gradual pressure equalization through the vacuum adjustment control 146c's connection to the atmosphere. Electronic processor 170 then translates nozzle 147 in a direction parallel to arrow 147b in FIG. 3B, e.g., in a direction away from channel 132. Chip 130 can then be removed from reader 100, for example.

In some embodiments, a positive pressure can be applied to channel 132 of chip 130 to initiate and/or sustain fluid flow through the channels of chip 130. The positive pressure can be produced by, for example, a positive displacement pump, a syringe pump, and/or other types of pumps. The pump can be fixed in position relative to support stage 120, or the pump can be movable, and can be moved into engagement with channel 132 in the manner described above for nozzle 147, for example.

In some embodiments, the pressure in the channels of chip 130 where nozzle 147 is connected is reduced to 60 kPa or less (e.g., 55 kPa or less, 50 kPa or less, 40 kPa or less, 30 kPa or less, 20 kPa or less, 15 kPa or less, 10 kPa or less, 8 kPa or less, 6 kPa or less).

In certain embodiments, a fluid flow rate in the channels of chip 130, in response to the pressure differential introduced via nozzle 147, is 50 µL/min or more (e.g., 100 µL/min or more, 200 µL/min or more, 300 µL/min or more, 400 µL/min or more, 500 µL/min or more, 600 µL/min or more, 800 µL/min or more, 1000 µL/min or more).

3. Actuator-Based Fluid Control System

The actuator control system is used to regulate fluid flow in the various channels of chip 130. As discussed above, chip 130 generally includes a plurality of fluid channels formed in a deformable material layer. Fluid flows through the channels according to a pressure differential introduced by the vacuum control system. To control the rate of fluid flow through the channels (including preventing fluid flow through certain channels at certain times), the actuator control system uses multiple actuators that function as channel regulator valves.

FIG. 4A shows a schematic diagram of actuator control module 140. Control module 140 includes a controller 141 connected to an actuator 142. Controller 141 is in electrical communication with electronic processor 170 via control line 172d. Actuator 142 is positioned above a channel 132 formed in chip 130. Chip 130 has a sandwich-type structure that includes a glass layer 136 and a layer 134 of a deformable material in which channel 132 has been formed. In general, a wide variety of materials, including various polymers and plastics can be used to form layer 134. Exemplary materials include elastomers such as polydimethylsiloxane, fluorosilicones, other fluoroelastomers (e.g., Viton®), and styrene-butadiene copolymer, polymethylmethacrylate, polydimethylacrylate.

In general, layer 134 can be formed from a material that has relatively high elasticity. For example, in some embodiments, the Young's modulus of the material that forms layer 134 can be 0.3 MPa or more (e.g., 1 MPa or more, 5 MPa or more, 10 MPa or more, 20 MPa or more, 40 MPa or more, 60 MPa or more, 80 MPa or more, 100 MPa or more).

Typically, layer 136 is formed from a material such as glass that is relatively inelastic and relatively optically clear. For example, in certain embodiments, the Young's modulus of the material that forms layer 136 can be 90,000 MPa or less (e.g., 60,000 MPa or less, 30,000 MPa or less, 20,000 MPa or less, 10,000 MPa or less, 5000 MPa or less, 3000 MPa or less, 1000 MPa or less).

In the open configuration shown in FIG. 4A, fluid can flow through channel 132 under the influence of the pressure differential in the channels of chip 130. To prevent fluid flow through channel 132, electronic processor 170 instructs controller 141 to translate actuator 142 in the direction of arrow 142a. As actuator 142 is translated, it first contacts the upper surface of chip 130. As actuator 142 is further translated, it begins to compress layer 134, closing off the interior region of channel 132. The extent to which actuator 142 is advanced in the direction of arrow 142a determines the available open space in channel 132 for fluid transport. Actuator 142 can be advanced far enough that channel 132 is completely closed off to fluid transport, as shown in FIG. 4B.

Typically, actuator control module 140 includes a plurality of actuators 142 and electronic processor 170 can control fluid transport through multiple channels of chip 130 at the same time. For example, electronic processor 170 can introduce one or more samples, one or more solutions of tagging agents, one or more buffer and/or washing solutions, and various other types of solutions into different regions of chip 130 at controlled times. Further, by regulating the extent to which each actuator collapses its corresponding fluid channel, the fluid flow rate through each channel can be controlled.

In general, actuators 142 are positioned above stage 120 and chip 130 when chip 130 is inserted into reader 100. As discussed above in connection with nozzle 147, when chip 130 is inserted, electronic processor 170—either automatically in response to a signal from sensor 128, or in response to a manual signal from a system operator entered via display interface 190—can initiate downward motion of actuators 142, so that the actuators come to rest just above the surface of chip 130, or in gentle contact with the surface of chip 130, or in a position that applies sufficient pressure to the deformable layer 134 of chip 130 such that an underlying channel is blocked to fluid flow (e.g., the channel is in a "normally closed" configuration). In some embodiments, when chip 130 is inserted, a system operator manually closes the door covering access port 200. The door is mechanically linked to a mechanism which lowers actuators 142 onto chip 130. The action of closing the door lowers actuators 142. Thereafter, electronic processor 170 can control the extent to which each of the corresponding channels of chip 130 are closed off by selectively extending actuators 142.

Figure 5A:
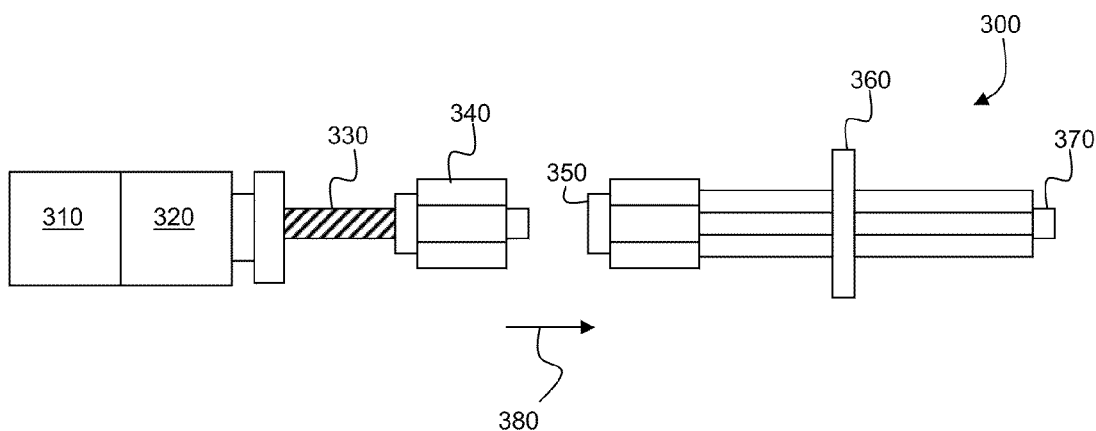
FIG. 5A is a schematic diagram of a motorized actuator.

A variety of different types of actuators can be used in reader 100. In some embodiments, for example, motorized actuators can be used. FIG. 5A shows a schematic diagram of a motorized actuator 300 that can be used for fluid flow control in reader 100. Actuator 300 includes a DC motor 310, a gearbox 320, a spring 330, a drive nut 340, an o-ring 350, an actuator stop 360, and a channel pin 370. Motor 310 is electrically connected to controller 141, as discussed above. To extend actuator 300, controller 141 sends a control signal that activates DC motor 310. Motor 310 delivers torque along a rotating shaft to gearbox 320, which adjusts the gear-ratio of the motor (e.g., in some embodiments, gearbox 320 provides a 1:256 gear ratio). Gearbox 320 includes a second rotating shaft that is threaded through drive nut 340. Drive nut 340 is prevented from rotating by an actuator mount assembly (not shown in FIG. 5A) that encloses components of actuator 300, but can freely move in the vertical direction 380. When motor 310 is activated, the second rotating shaft in gearbox 320 rotates, moving drive nut 340 downward in FIG. 5A toward o-ring 350. O-ring 350 is connected via a continuous member to channel pin 370. When drive nut 340 applies a force to o-ring 350, channel pin 370 moves downwards in the direction of arrow 380. The compression of deformable material layer 134 on chip 130 results in a force anti-parallel to arrow 380 which is transmitted to the motor 310. Motor 310 increases the current draw to continue rotating against the compression force. The motor current is detected by the controller 141 and when the current rises above a threshold corresponding to full compression of layer 134, motor 310 is stopped. Actuator stop 360 is positioned to prevent channel pin 370 from extending too far in the direction of arrow 380 and damaging chip 130. O-ring 350 is formed of a compressible material. In the absence of chip 130 (e.g., with no chip inserted), prior to encountering a "hard stop" against actuator stop 360, drive nut 340 compresses o-ring 350, increasing the current draw of motor 310 and signaling the motor to stop.

To withdraw actuator 300, controller 141 sends a control signal to motor 310 that causes motor 310 to rotate in the opposite direction. The second rotating shaft in gearbox 320 is rotated in the opposite direction, so that drive nut 340 moves in a direction opposite to arrow 380. With drive nut 340 no longer exerting a downward compressive force on o-ring 350, the natural elasticity of the deformable material that forms layer 134 exerts an upward force (e.g., anti-parallel to arrow 380) on channel pin 370, moving the pin in the opposite direction to arrow 380. As a result, the channel that had been partially compressed by channel pin 370 returns, as actuator 300 is progressively withdrawn, toward its original cross-sectional shape and re-opens to permit fluid flow once again. Spring 330 is positioned so that as drive nut 340 approaches gearbox 320, the drive current of motor 310 will increase and signal the motor to stop as described above.

Figure 5E:
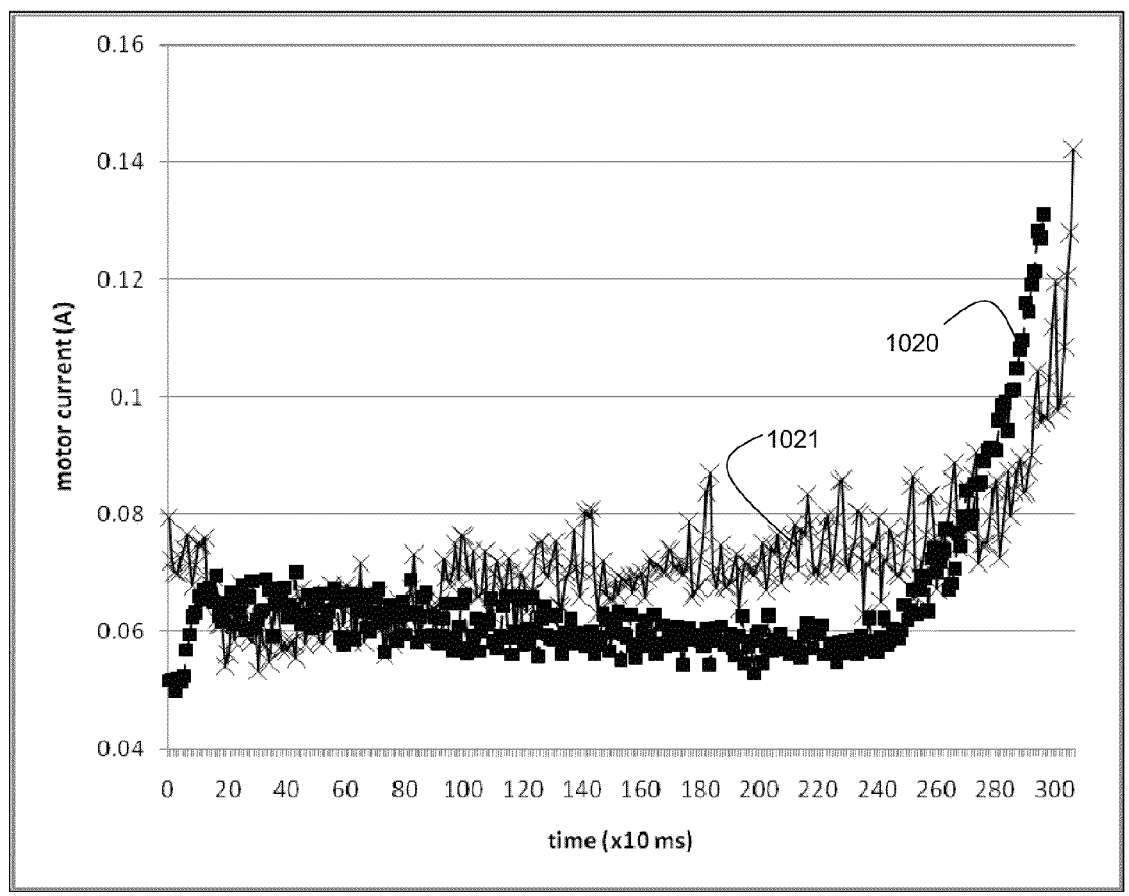
FIG. 5E is a plot showing motorized actuator current as a function of time for an open-close cycle of the actuator.

As discussed above in connection with the vacuum control system, o-ring 350 provides a force-feedback indicator for electronic processor 170 that allows processor 170 to determine the extent to which the channel under actuator 300 has been closed off by the actuator. As nut 340 applies force to o-ring 350 causing compression of o-ring 350, the elastic force of o-ring 350 that opposes its compression increases. To cause further translation of channel pin 170, electronic processor 170 (via controller 141) must supply a larger drive current to motor 310. When this current reaches a threshold value, electronic processor 170 determines that the channel underlying actuator 300 has been closed. Even before the channel has been closed, however, electronic processor 170 can determine the extent to which the channel has been closed by measuring the drive current supplied to motor 310. FIG. 5E shows a plot of motorized actuator current as a function of time for one open cycle 1020 and one close cycle 1021 of an actuator. With careful selection of the threshold current, this simple control scheme can assure that the total distance traveled in each open-close cycle is highly reproducible, with a variation of less than 7% over multiple cycles and multiple actuators. This repeatability can be important in some embodiments to avoid applying excessive pressure to the chip, especially if the chip is made of a fragile material such as glass.

In general, a wide variety of different actuators can be used. FIG. 5B shows an embodiment of an actuator 301 that includes a flat, geared disc 1001 with several patterns of pins or protrusions 1002 on one face. The pins close off microfluidic channels when positioned above the channels appropriately. The pattern of pins on the geared disc corresponds to a selected valve configuration. Disc 1001 is positioned relative to the channels such that the different pins 1002 can close the channels when disc 1001 is lowered and rotated.

Disc 1001 is mounted on a vertical axle 1003 and rotation of the disc is accomplished via a system of gears 1004 connected to a motor, such as a stepper or servo motor 1005. The gear system can permit rotation of disc 1001 with a high degree of precision without requiring the use of a high-precision motor.

Vertical axle 1003 is connected to a mechanism that can move vertically a distance sufficient to allow a microfluidic chip 1006 to be inserted below disc 1001. For example, in some embodiments, the vertical motion of axle 1003 can be controlled via the horizontal motion of a linear actuator 1007 and a lever system. The overall mechanism can apply enough pressure to completely pinch off the microfluidic channels of chip 1006. In some embodiments, for example, each of pins 2002 can apply at least 200 g (e.g., at least 300 g of force, at least 400 g of force, at least 500 g of force, at least 600 g of force, at least 800 g of force, at least 1000 g of force) to chip 1006.

Typically, during use, the microfluidic chip 1006 is placed under disc 1001. Disc 1001 is then rotated by motor 1005 so that a particular pin configuration on the disc aligns with a pattern of channels in chip 1006. Disc 1001 is then lowered via actuator 1007 onto chip 1006, so that pins 1002 close off selected channels in chip 1006. To initiate a microfluidic operation (e.g., to transport fluid through one or more channels of chip 1006), a vacuum control module (e.g., vacuum control module 145) establishes a fluid connection with the channels of chip 1006, reducing the pressure in the channels to initiate fluid movement through the channels. After fluid motion is complete, vacuum control module 145 is disengaged, and disc 1001 is raised above chip 1006 by actuator 1007. The foregoing procedure is repeated for each movement of fluid through chip 1006. In certain embodiments, disc 1001 can be replaced with another disc that includes a different pattern of pins 1002, to permit operation with chips 1006 having different channel configurations.

FIG. 5C shows another embodiment of an actuator 302 that can be used in the systems disclosed herein. The actuator in FIG. 5C includes a plurality of pins 1008, each positioned over a microfluidic channel of a chip. Each of pins 1008 is mounted on a separate one of a plurality of springs 1009. Each of springs 1009 applies sufficient pressure to completely close off the microfluidic channels in the chip. For example, in some embodiments, each of pins 1008 connected to a corresponding spring 1009 can apply at least 200 g of force (e.g., at least 300 g of force, at least 400 g of force, at least 500 g of force, at least 600 g of force, at least 800 g of force, at least 1000 g of force) to the chip.

Camshaft 1010 includes one cam for each combination of a pin 1008 and a spring 1009. Each of the cams on shaft 1010 can include one lobe or more than one lobe, and each cam can be oriented differently or in the same manner around shaft 1010. Camshaft 1010 is rotated by a stepper or servo motor, for example (not shown in FIG. 5C). During use, shaft 1010 is first rotated so that all pins 1008 are in a raised position, where none of pins 1008 would contact a microfluidic chip positioned under the pins. A chip is then inserted under the pins, and camshaft 1010 is rotated so that all pins 1008 are lowered into contact with the chip, thereby closing all channels positioned below pins 1008 in the chip. Vacuum control module 145 then engages with the channels of the chip to form a reduced pressure environment within the channels. Camshaft 1010 is rotated, opening certain channels in the chip and permitting fluid to flow through certain channels in a controlled manner. After the fluid flow operation has completed, camshaft 1010 is again rotated to close off all fluid channels, halting fluid flow in the chip. To initiate further fluid flows, camshaft 1010 can be rotated to select particular configurations of pins 1008 (e.g., by rotating camshaft 1010, certain pins 1008 are raised, opening channels in the chip, and certain pins 1008 remain lowered, keeping corresponding channels in the chip closed). Thus, fluid transport through the chip can be efficiently achieved. In some embodiments, camshaft 1010 can be replaced by one or more different camshafts that permit alternate pin configurations to be used, permitting use of camshaft 1010 with chips having different channel arrangements and enabling different configurations of open and closed channels in the chips. As the closing force is provided by spring 1009, this embodiment requires very little power to operate; the only power required is the power needed to rotate the stepper or servo motor when the pin positions are changed.

Figure 5D:
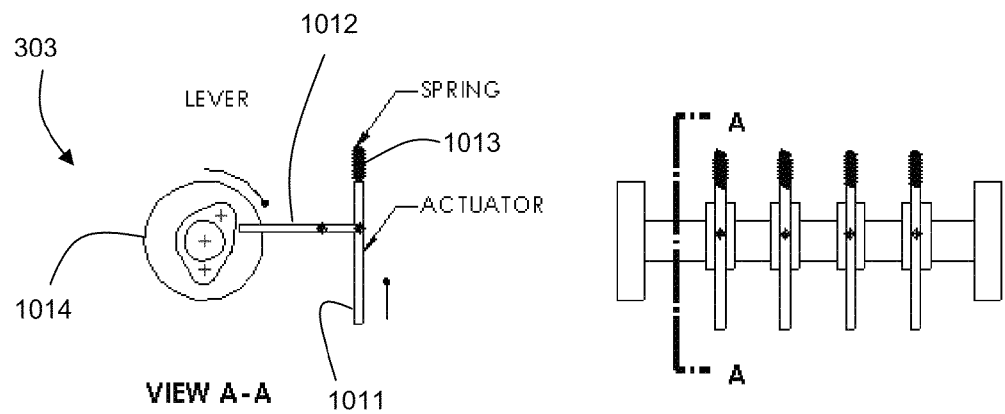
FIG. 5D is a schematic drawing of a cam and coil-spring actuator.
Figure 5D:
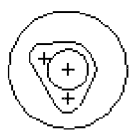

FIG. 5D shows a further embodiment of an actuator 303 that can be used in the systems disclosed herein. Actuator 303 includes a plurality of pins 1011, each positioned over a microfluidic channel in a chip. Each pin 1011 is mounted on a corresponding lever 1012 and connected to a corresponding spring 1013. Each of springs 1013, in combination with pins 1011, applies enough pressure to completely close off a corresponding channel in the chip. For example, in some embodiments, each combination of spring 1013 and pin 1011 applies at least 200 g (e.g., at least 300 g of force, at least 400 g of force, at least 500 g of force, at least 600 g of force, at least 800 g of force, at least 1000 g of force) to the chip.

Ordinarily, pins 1011 and springs 1013 close off the channels of the chip. Camshaft 1014 includes one cam for each combination of a spring 1013, a lever 1012, and a pin 1011. Each individual cam on camshaft 1014 can include one lobe, or more than one lobe. Each of the cams can be oriented differently or in the same manner around shaft 1014. Typically, for example, camshaft 1014 is rotated by a servo or stepper motor.

During use, shaft 1014 is first rotated so that all pins 1011 are in a raised position, where none of pins 1011 would contact a microfluidic chip positioned under the pins. A chip is then inserted under the pins, and camshaft 1014 is rotated so that all pins 1011 are lowered into contact with the chip, thereby closing all channels positioned below pins 1011 in the chip. Vacuum control module 145 then engages with the channels of the chip to form a reduced pressure environment within the channels. Camshaft 1014 is rotated, opening certain channels in the chip and permitting fluid to flow through certain channels in a controlled manner. After the fluid flow operation has completed, camshaft 1014 is again rotated to close off all fluid channels, halting fluid flow in the chip. To initiate further fluid flows, camshaft 1014 can be rotated to select particular configurations of pins 1011. Thus, fluid transport through the chip can be efficiently achieved. In some embodiments, camshaft 1014 can be replaced by one or more different camshafts that permit alternate pin configurations to be used, permitting use of camshaft 1014 with chips having different channel arrangements and enabling different configurations of open and closed channels in the chips. As the closing force is provided by the spring 1009, this embodiment can operate with very little power (e.g., only the amount of power needed to rotate the stepper or servo motor when the pin positions are changed).

In certain embodiments, solenoid-based actuators can be used. Solenoid-based actuators include a coil element that can be activated by passing an electrical current through the coil, and a movable magnetic element positioned at least partially within the interior region of the coil. When electronic processor 170 supplies a current to the coil, an induced magnetic field at the center of the coil applies a magnetic force to the movable element, causing the element to extend from the coil center. The movable element is connected to a channel pin, which closes off a fluid channel in chip 130 as discussed above. The larger the current supplied by electronic processor 170 to the coil, the larger the force on the movable element, and the larger the force applied by the channel pin to the wall of the fluid channel. Thus, by controlling the applied coil current, electronic processor 170 can control the extent to which the fluid channel is closed to fluid flow.

Typically, reader 100 includes four actuators, each of which regulates fluid flow in a different channel of chip 130. As an example, one of the four actuators can control fluid flow from a reservoir region of chip 130 containing the sample to the analysis region. Another of the four actuators can control fluid flow from a reservoir containing a solution of tagging agent to the analysis region. Yet another of the four actuators can control fluid flow from a reservoir containing a buffer and/or wash solution to the analysis region. The final actuator can control fluid flow from another reservoir containing another buffer solution, a solution of another tagging agent, water, a primary binding agent (e.g., an antibody-based binding agent), another type of solution, or atmospheric air to the analysis region.

Figure 6:
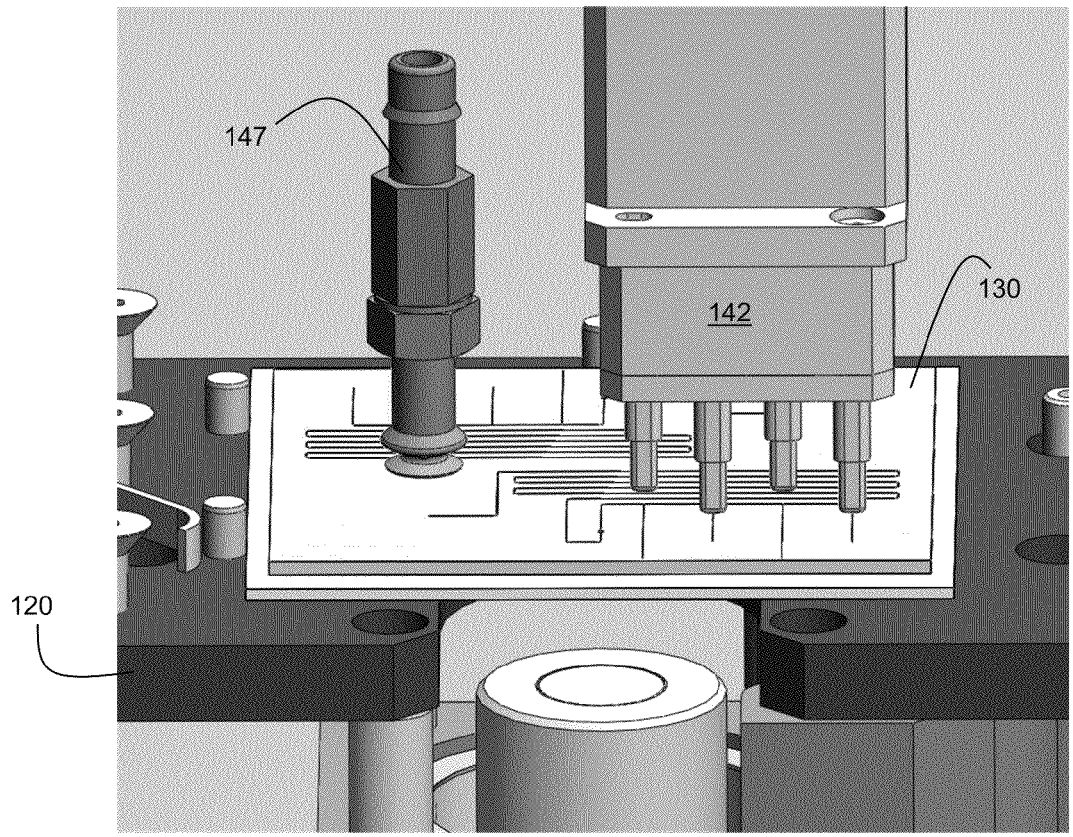
FIG. 6 is a schematic diagram showing a vacuum nozzle and actuators engaged with a surface of a chip.

FIG. 6 shows a schematic diagram of an actuator block that includes four actuators 142 positioned to control fluid flow through channels of a chip 130. Although in the foregoing description each actuator was generally used to control flow through a single channel in chip 130, more generally, each actuator can be used to control fluid flow through one or more channels of chip 130, depending upon the cross-sectional width of the channels and the diameter of each channel pin 170. In certain embodiments, for example, by using a large-diameter channel pin, an actuator can be used to reversibly close and open multiple fluid channels at once.

In some embodiments, reader 100 includes more than four actuators. For example, in certain embodiments, reader 100 includes five or more actuators (e.g., six or more actuators, seven or more actuators, eight or more actuators, ten or more actuators, twelve or more actuators). The additional actuators can be used to control the flow of additional buffer/washing solutions, solutions of additional binding agents, solutions of additional tagging agents, solutions of chemically reactive agents, and solutions of additional samples on chip 130 (e.g., in embodiments where chip 130 includes reservoirs for multiple samples, each of which can be analyzed by reader 100).

In certain embodiments, the travel distance of channel pin 370 (e.g., in a direction parallel to arrow 380) is 0.01 mm or more (e.g., 0.05 mm or more, 0.01 mm or more, 0.05 mm or more, 0.1 mm or more, 0.5 mm or more, 1.0 mm or more, 2.0 mm or more, 3.0 mm or more, 5.0 mm or more). In certain embodiments, the rate of extension of channel pin 370 (e.g., in a direction parallel to arrow 380) is 0.02 mm/s or more (e.g., 0.04 mm/s or more, 0.06 mm/s or more, 0.08 mm/s or more, 0.10 mm/s or more, 0.12 mm/s or more, 0.14 mm/s or more, 0.16 mm/s or more, 0.18 mm/s or more, 0.20 mm/s or more, 0.3 mm/s or more, 0.4 mm/s or more, 0.5 mm/s or more, 0.6 mm/s or more, 0.7 mm/s or more, 0.8 mm/s or more, 1.0 mm/s or more). In some embodiments, the pressure applied by channel pin 370 to chip 130 is 1.0 kPa or more (e.g., 2.0 kPa or more, 5.0 kPa or more, 10.0 kPa or more, 20.0 kPa or more, 30.0 kPa or more, 50.0 kPa or more, 100 kPa or more, 200 kPa or more, 400 kPa or more, 600 kPa or more, 800 kPa or more, 1000 kPa or more).

The preceding discussion provides exemplary fluid propulsion and fluid control systems that can be implemented in molecular reader 100. More generally, however, a wide variety of different types of fluid propulsion and control systems can be implemented. Further examples of fluid propulsion and control in channels of microfluidic chips, any one or more of which can be implemented in molecular reader 100, are disclosed in: U.S. patent application Ser. No. 11/875,031, now published as U.S. Patent Application Publication No. US 2009/0032399; and Wang, J. et al., "Microfluidic Cell Electroporation Using a Mechanical Valve," *Analytical Chemistry* 79: 9584-9587 (2007). The entire contents of each of the foregoing publications and patent applications are incorporated herein by reference.

4. Radiation Source/Detection System

Molecular reader 100 can use a variety of different radiation sources. In some embodiments, for example, radiation source 150 can include one or more light-emitting diodes (LEDs). In certain embodiments, radiation source 150 can include one or more laser diodes and/or one or more laser sources (e.g., gas and/or solid state lasers). In some embodiments, radiation source 150 can include one or more broad-spectrum sources such as lamps or blackbody emitters. In some embodiments, radiation source 150 can include one or more incoherent sources such as flashlamps. Source 150 can include continuous wave and/or pulsed sources, which can be operated synchronously with a time-gated detection device to reduce noise and/or background contributions to measured signals. Typically, LEDs consume relatively little power and provide high-efficiency excitation light, and are therefore advantageous for use in reader 100. In some embodiments, a radiation source can be positioned relative to the other optics to enable bright-field imaging of the chip. The bright-field image can be formed by either transmission of the light through the chip or by illumination of the chip from the same side as the detector.

Molecular reader 100 can also include one or more of a variety of different types of detectors. Typically, reader 100 includes at least one type of imaging detector such as, for example, a CCD camera, a CMOS camera, a film-based camera, or an array detector based on photodiodes. Detector 160 can also include one or more of a variety of different types of non-imaging detectors such as, for example, photodiodes, photomultiplier tubes, and other such devices.

In some embodiments, detector 160 is a CCD camera. In one embodiment, the CCD camera is designed around a CCD sensor with high sensitivity and low readout noise when run at room temperature, i.e. 20-30 degrees C. Use of a sensor with these characteristics allows images to be acquired with a high signal-noise-ratio without the use of thermoelectric cooling and ensuing high power consumption. The camera electronics are designed to take up a small amount of space, in order to reduce the overall footprint of the reader 100. The CCD camera may, for example, have a dimensions of 8.9 mm by 6.35 mm. Some embodiments can be smaller in size.

Reader 100 can include a variety of different optical elements that operate in connection with source 150 and/or detector 160 to provide excitation light to the sample in chip 130, and to collect emitted light from the sample. For example, in some embodiments, reader 100 can include one or more narrowband optical filters positioned to prevent excitation light from source 150 from reaching detector 160. In certain embodiments, reader 100 can include one or more beamsplitters (e.g., one or more dichroic beamsplitters) that are used to combine radiation generated by different radiation sources (e.g., multiple LEDs) into a single beam of incident radiation. The beamsplitters can also function as filters to reduce the intensity of incident radiation that reaches detector 160.

In some embodiments, reader 100 can include one or more lenses. Lenses can be configured, for example, to focus incident radiation onto a portion of chip 130 where an analyte of interest is bound (e.g., in an analysis region of chip 130). Lenses can also be configured to image the analysis region, or a portion thereof, onto an active element of detector 160, such as the array of a CCD camera. By detecting fluorescence emitted from the tagged analyte molecules, the sample of interest can be identified and/or quantified.

Reader 100 can also include any of a variety of other optical elements that are commonly used in optical excitation and/or detection systems. For example, reader 100 can include one or more lenses, mirrors, beamsplitters, dispersive elements such as gratings, prisms and wedges, nonlinear optical crystals, and various polarization-sensitive elements such as waveplates and polarizers. A wide variety of different optical configurations can be implemented in reader 100.

Figure 7A:
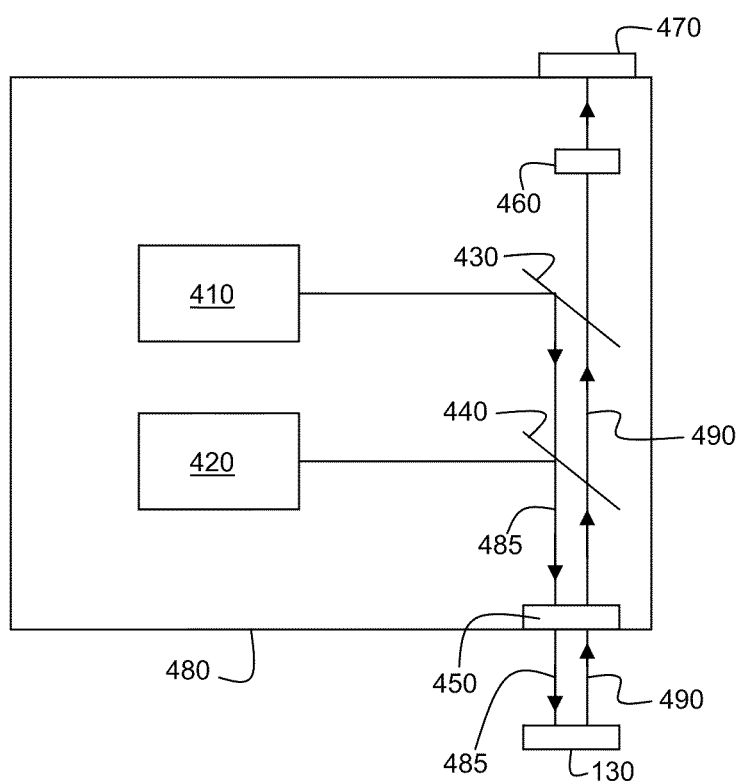
FIG. 7A is a schematic diagram showing an embodiment of an optical system of a molecular reader.

An exemplary configuration of optical elements 400 in reader 100 is shown in FIG. 7A. Some of the various elements shown in FIG. 7A are packaged within a single light-impermeable housing 480. Housing 480 includes two LED radiation sources 410 and 420. Dichroic beamsplitters 430 and 440 can be positioned, for example, at a 45 degree angle to the output of radiation sources 410 and 420, and can combine output radiation from sources 410 and 420 to form incident radiation 485 that is directed by lens 450 onto a region of chip 130. The illuminated region of chip 130 can include fluorescent tag molecules if the analyte of interest was present in the sample contained in chip 130. Emitted radiation 490 leaves chip 130, passes through beamsplitters 430 and 440 and filter 460 which filter out incident radiation 485, and is detected by CCD camera 470 which is mounted in an aperture of housing 480. Beamsplitters 430 and 440 are typically designed to that they efficiently transmit the wavelengths of light emitted by the fluorescent tags excited by radiation sources 410 and 420. In addition, beamsplitter 430 is transmissive at the wavelength of light produced by source 420. In some embodiments, beamsplitter 430 transmits with high efficiency (e.g., transmitted light intensity of 95% or more of the input light intensity) all wavelengths longer than 575 nm, while beamsplitter 440 transmits with high efficiency wavelengths between 575 nm and 598 nm, and wavelengths longer than 673 nm. FIGS. 7D and 7E, respectively, are plots showing transmitted light intensity as a function of wavelength for embodiments of beamsplitters 430 and 440. In general, the entire sealed package enclosed within housing 480 can be mounted as a single unit in molecular reader 100. In certain embodiments, the size of the packaged unit is 110 mm×110 mm×95 mm and weighs less than 1 pound. The size of the packaged unit allows it to be easily transported. Some embodiments can be smaller in size and/or weight.

Figure 7B:
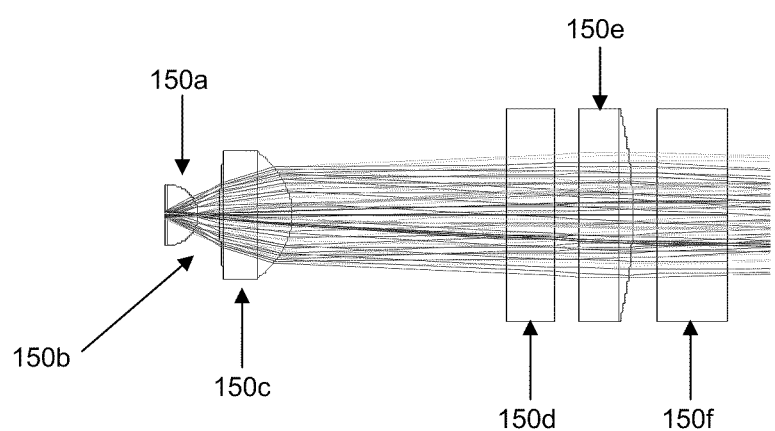
FIG. 7B is a schematic diagram showing an embodiment of a radiation source.
Figure 7C:
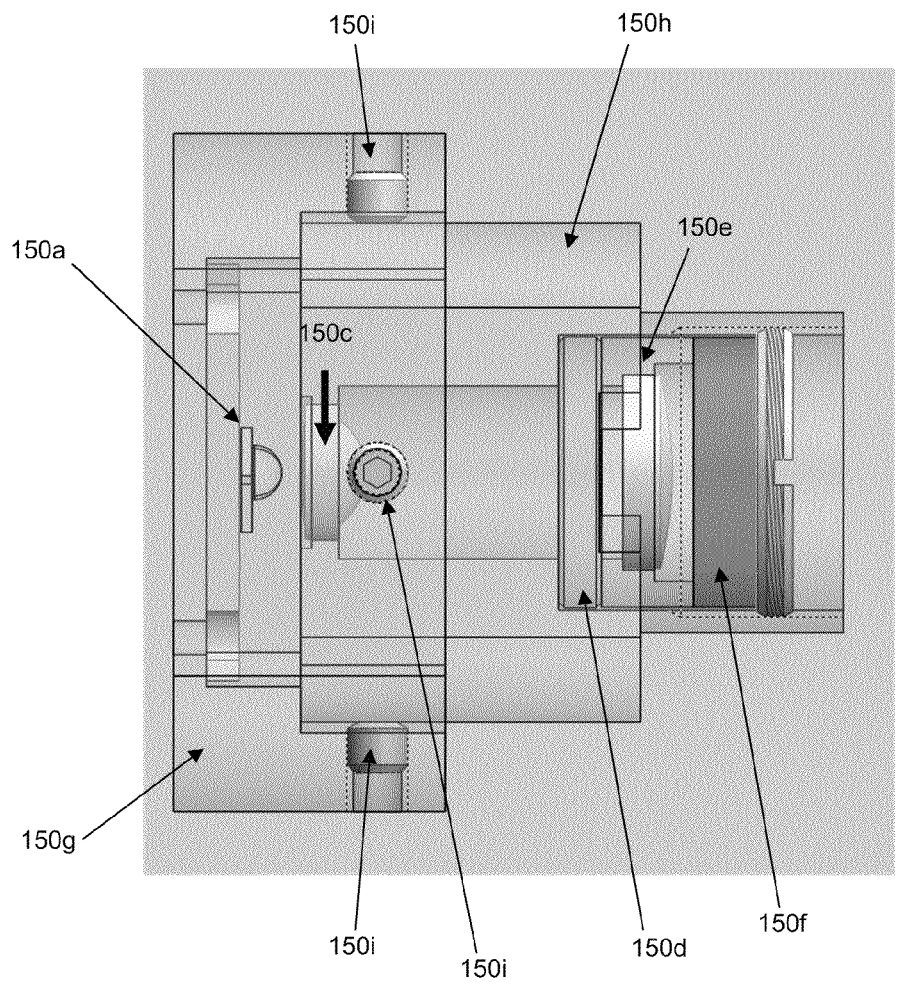
FIG. 7C is a schematic diagram showing a portion of a radiation source.
Figure 7D:
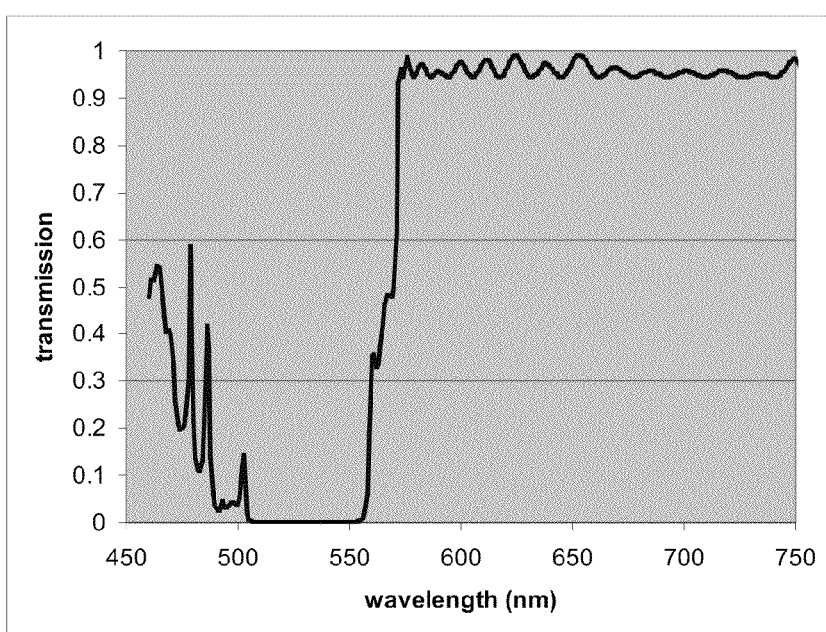
FIGS. 7D and 7E are plots of transmitted light intensity as a function of wavelength for embodiments of two different beamsplitters used in a radiation source assembly.
Figure 7E:
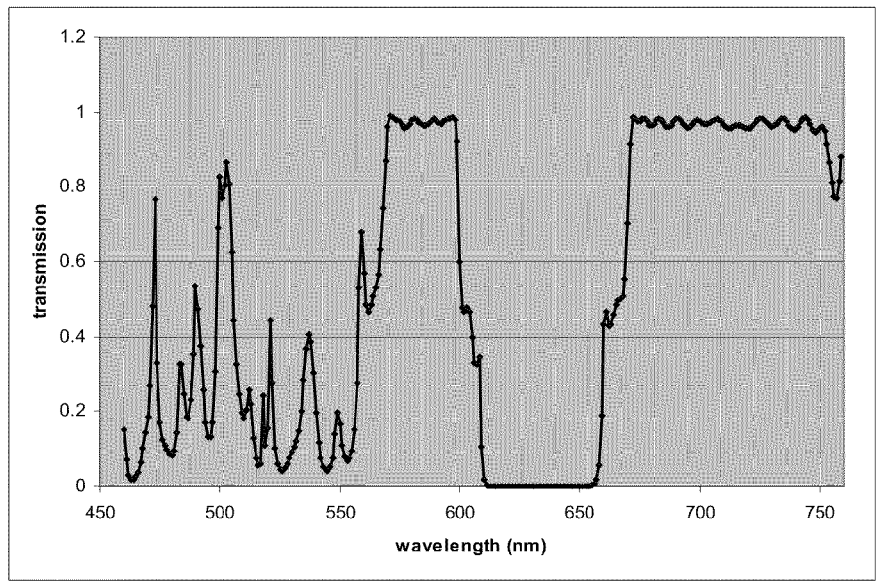
Figure 7F:
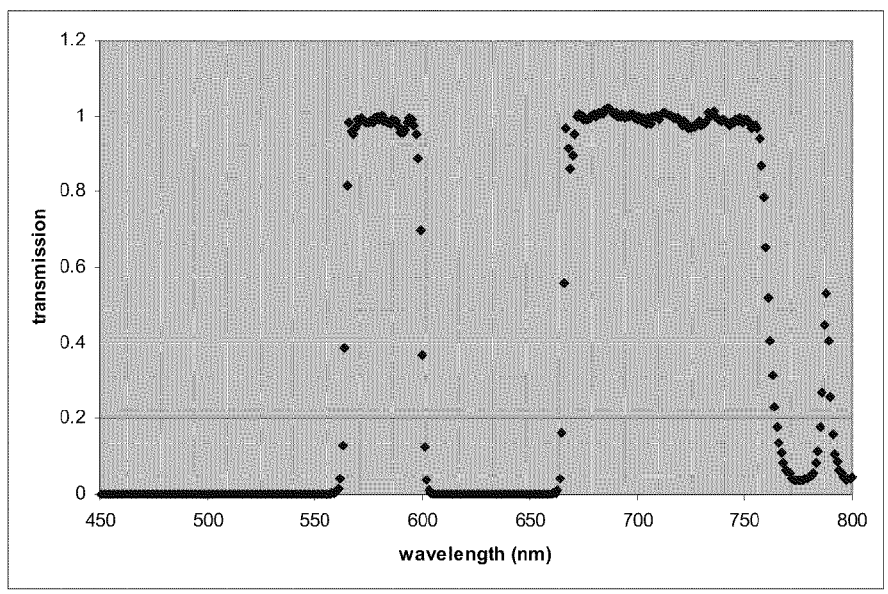
FIG. 7F is a plot of transmitted light intensity as a function of wavelength for an embodiment of an emission filter used in a radiation source assembly.

FIG. 7B shows an exemplary embodiment of a radiation source 150. Source 150 includes a light-emitting diode 150a that emits incoherent light 150b that is received by collection lens 150c. Light 150b is collimated by lens 150c and subsequently passes through filter 150d to narrow its spectral width. Light 150b then passes through imaging lens 150e which images light 150b to a selected point relative to the rest of the optical system such that the intensity of light 150b is relatively even across the cross-sectional field of view of the reader. A secondary filter 150f can be used to further remove particular wavelengths of light emitted by LED 150a, such as near-ultraviolet or near-infrared wavelengths. Referring to FIG. 7C, in some embodiments LED 150a can be mounted in housing 150g, and the other components 150c-150g can mounted in housing 150h. The position of LED 150a relative to collection lens 150c can be adjusted using four set screws 150i (three of which are shown in FIG. 7C). In certain embodiments, the optical power of the illumination light that is incident on the chip can be 0.1 mW or more (e.g., 0.5 mW or more, 1.0 mW or more, 2.0 mW or more, 5.0 mW or more, 10.0 mW or more, 20.0 mW or more, 30.0 mW or more, 50.0 mW or more, 70.0 mW or more, 100 mW or more).

The reader 100 can include an objective lens assembly. In some embodiments, the objective lens assembly serves to focus radiation from source 150 onto an area of the chip 130. In other embodiments the objective lens assembly also magnifies the image of an area of the chip 130 for imaging by the detector. In some embodiments, a magnifying power of the objective lens assembly is 50× or more (25× or more, 10× or more, 5× or more). In some embodiments, a numeric aperture of the optical system of reader 100 is 0.2 or more (e.g., 0.3 or more, 0.4 or more, 0.5 or more, 0.6 or more, 0.7 or more, 0.8 or more, 0.9 or more, 1.0 or more). With a larger numeric aperture, a wider field of view on the surface of chip 130 can be captured in images measured by detector 160.

In certain embodiments, a depth of focus of the optical system of reader 100 is 0.1 micron or more (e.g., 0.2 micron or more, 0.3 micron or more, 0.4 micron or more, 0.5 micron or more, 0.6 micron or more, 0.7 micron or more, 0.8 micron or more, 0.9 micron or more). In some embodiments, the depth of focus is 50 microns or less (e.g., 40 microns or less, 30 microns or less, 20 microns or less, 10 microns or less, 8.0 microns or less, 6.0 microns or less, 4.0 microns or less, 3.0 microns or less, 2.5 microns or less, 2.0 microns or less, 1.5 microns or less).

Generally, the central wavelength(s) of excitation radiation provided by radiation source 150 is/are selected for efficient excitation/absorption by molecules in the sample of interest, and/or for efficient detection by detector 160. For example, when components of the sample are tagged with fluorescence emitting tagging agents, incident radiation having a central wavelength within the visible region of the electromagnetic spectrum can be generated by source 150. In some embodiments, source 150 can include multiple radiation emitters (e.g., multiple LEDs), each of which emits radiation in a selected region of the electromagnetic spectrum. For example, source 150 can include two LEDs, one of which emits incident radiation at a central wavelength of about 535 nm which is suitable for exciting fluorescent tagging agents Cy3, AlexaFluor 532 (available from Life Technologies Corporation, Carlsbad, Calif.), AlexaFluor 555, and similar tagging agents, while the other emits incident radiation at a central wavelength of 635 nm which is suitable for exciting fluorescent tagging agents Cy5, AlexFluor 647 (available from Life Technologies Corporation, Carlsbad, Calif.), and other similar tagging agents.

In general, the full-width at half-maximum bandwidth of the incident radiation emitted by source 150 can be 0.01 nm or more (e.g., 0.02 nm or more, 0.04 nm or more, 0.06 nm or more, 0.08 nm or more, 0.10 nm or more, 0.15 nm or more, 2.0 nm or more, 5.0 nm or more, 10.0 nm or more, 20.0 nm or more) and/or 500 nm or less (e.g., 450 nm or less, 400 nm or less, 350 nm or less, 300 nm or less, 250 nm or less, 200 nm or less, 150 nm or less, 100 nm or less, 50 nm or less).

In certain embodiments, the optical system of reader 100 can include a thin film emission filter (e.g., filter 460) configured to further decrease the amount of stray excitation light that is detected by detector 160. FIG. 7E shows a plot of transmission intensity as a function of wavelength for an exemplary embodiment of such an emission filter. The filter effectively filters out wavelengths of radiation in the visible region of the electromagnetic spectrum, except for wavelengths between about 575 nm and about 598 nm, and wavelengths longer than about 673 nm.

In some embodiments, the optical system of reader 100 can include an autofocus mechanism to permit adjustment of the system's imaging properties for different chips 130. Referring again to FIG. 7, lens 450 (which can include one or more optical elements such as lenses, filters, mirrors, and other elements) forms an objective lens assembly that images chip 130 onto CCD detector 470. To permit examination of different chips 130, objective lens 450 can be mounted on a movable, autofocusing stage, which permits movement of lens 450 parallel to the direction of arrow 495.

FIG. 8 shows a schematic diagram of an autofocusing assembly 500 that permits automated adjustment of the position of objective lens 450 with respect to chip 130. Assembly 500 includes a stepper-driven motor 510 in electrical communication with electronic processor 170, and objective lens 450 connected to an arm 520 which pivots about a pivot member 530. To adjust the focus of the optical system, electronic processor 170 issues control instructions which cause motor 510 to either extend or retract shaft 515. As shaft 515 extends in the +z direction, for example, the right end of arm 520 moves downward in FIG. 8. Because arm 520 pivots around pivot member 530, the downward motion of the right end of arm 520 leads to upward motion (e.g., in the −z direction) of the left end of arm 520 in FIG. 8. As a result, objective lens 450, which is connected to arm 520, also moves in the −z direction. To move objective lens in the +z direction, electronic processor 170 issues instructions to motor 510 to retract shaft 515 (e.g., to withdraw shaft 515 in the −z direction). The direction and magnitude of the control instructions are determined, for example, by acquiring an image of the chip and applying image processing algorithms, implemented in electronic processor 170, to evaluate the degree of focus of the image.

The combination of a high resolution stepper motor 510 and pivoting arm 520 yields an autofocusing assembly with sub-micron resolution. For example, in some embodiments, the position of objective lens 450 along the z direction can be adjusted in increments of 1.0 micron or less (e.g., 0.9 micron or less, 0.8 micron or less, 0.7 micron or less, 0.6 micron or less, 0.5 micron or less, 0.4 micron or less, 0.3 micron or less, 0.2 micron or less, 0.1 micron or less).

5. Thermal Control Module

The chemical reactions that occur when a sample is bound in the analysis region of chip 130 and tagged with one or more tagging agents are typically aided when the temperature of the sample is elevated above or reduced below room temperature. For example, in some embodiments, reader 100 and chip 130 are configured for a protein assay, in which particular proteins and/or molecular amino acid sequences in a sample are measured. Typically, the analysis region of chip 130 is functionalized with antigens that selectively bind the protein/sequence of interest. After the protein is bound to the corresponding antigens, a fluorescent tagging agent is introduced into the analysis region. The tagging agent selectively binds to the bound protein. In subsequent fluorescence imaging, the tagged proteins can be identified and quantified.

The rate of the binding reactions of the protein molecules and the tagging agents can typically be increased by raising the temperature of chip 130 to between about 37° C. and 40° C. To facilitate the control of temperature within chip 130, the chip can include one or more thermal elements that function both as heating elements and as temperature measurement devices. Use of the same element for both resistive heating and temperature measurement increases the number of elements need to be integrated on the chip and allows a larger number of independently-temperature-controlled regions on a given chip.

For example, in some embodiments, the heating element includes two exposed electrical contacts on a surface of chip 130. Thermal control module 135 is configured to interface with the electrical contacts of the heating element, providing both control over, and measurement of, the temperature in chip 130. FIG. 9A shows a schematic diagram of thermal control module 135. Module 135 includes contact pins 136 in engagement with a motorized controller 137. In certain embodiments, pins 136 are pogo pins (available, for example, from Everett Charles Technologies, Pomona, Calif.). The pogo pins are spring-loaded, and permit rapid and reliable electrical contact to be made with contacts 131a and 131b. Controller 137 is in electrical communication with electronic processor 170 via control line 172h.

When chip 130 is inserted into reader 100, electronic processor 170—either automatically in response to a signal from sensor 128, or in response to a manual signal entered by a system operator via display interface 190—activates controller 137. Controller 137 lowers pins 136 in the direction of arrow 138, until pins 136 contact electrical terminals 131a and 131b of thermal element 131 in chip 130. In some embodiments, when chip 130 is inserted, a system operator manually closes the door covering access port 200. The door is mechanically linked to a mechanism that lowers pins 136 onto terminals 131a and 131b. Therefore, the action of closing the door lowers pins 136.

FIG. 9B shows pins 136 in contact with terminals 131a and 131b. Thermal control module 135, when connected to thermal element 131, provides two different but related functions. First, thermal control module 135 can be used to monitor the temperature of chip 130 (and of the sample within chip 130). Thermal element 131 is selected such that its electrical resistance varies measurably with temperature. Thus, to measure the temperature of chip 130, electronic processor 170 directs a small measurement current to flow through one of pins 136, through thermal element 131, and through the other pin 136. From the voltage drop across thermal element 131 (or, alternatively, from the magnitude of the applied current at constant voltage through thermal element 131), electronic processor 170 can determine the electrical resistance of element 131. From the measured resistance of element 131, electronic processor can then determine the temperature of chip 130 (e.g., by referring to a resistance-temperature table and/or by calculating temperature from a pre-determined equation relating resistance and temperature Second, thermal control module 135 can be used together with thermal element 131 to heat chip 130 and the sample therein. As discussed above, heating chip 130 can increase the rate of various chemical reactions in the chip that are part of the analysis protocol therein. To heat chip 130, electronic processor 170 delivers a heating current, which in some embodiments maybe significantly larger than the measuring current, through pins 136 to thermal element 131. The resistance of thermal element 131 converts a portion of heating current to heat energy, which propagates into chip 130. As a result, electronic processor 170 can produce controlled, gradual heating of a localized area of chip 130 by controlling the magnitude of current delivered to thermal element 131. By monitoring the resistance of thermal element 131 at the same time, electronic processor 170 can heat chip 130 to a selected temperature, and at a selected temporal rate of temperature change.

In certain embodiments, thermal element 131 can be implemented as a small, inexpensive, low-resistance (e.g., 220 ohm) thermistor with a size of about 0.6 mm×0.6 mm×0.3 mm. Use of a single, small element to both raise and measure temperature consumes little surface area on chip 130, and permits many areas of a chip to be independently heated. Integration of thermal element 131 into chip 130 provides an area for efficient thermal transfer between chip 130 and thermal element 131. Because thermal element 131 can be implemented as a low cost device, chip 130 can be disposable following use, and system operators can process a large number of chips at relatively low cost.

In some embodiments, chip 130 can include more than one thermal element 131. For example, multiple thermal elements 131 can be used to measure and regulate temperatures either collectively or independently in various portions of chip 130. For example, in certain embodiments, the multiple thermal elements 131 in chip 130 can be electrically connected, so that the temperature in each of the chip regions adjacent to thermal elements 131 can be regulated collectively via application and measurement of suitable voltages via pins 136. In some embodiments, reader 100 includes multiple pairs of pins 136, each of which is actuated to make contact with one or more thermal elements 131 in chip 130 in the manner discussed above upon insertion of chip 130 into reader 100. Each pair of pins 136 can be used to measure and regulate temperature in one or more regions of chip 130 by applying and measuring suitable voltages across the pins. In this manner, independent temperature measurement and regulation in different portions of chip 130 can be achieved.

6. Display and Communications Interfaces

Referring again to FIG. 1, molecular reader 100 includes a display interface 190 in electrical communication with electronic processor 170. Display interface 190 can include, for example, a display screen such as a liquid crystal display screen. The display screen can be configured to display information to a system operator, including information about assays in progress, information about reader 100's configuration, information about the sample in chip 130, and other operating and/or status information.

In some embodiments, display interface 190 can also include an input interface that allows a system operator to enter commands and/or information. For example, display interface 190 can include a touch-screen interface that permits both the display of information and the entry of information. Alternatively, or in addition, display interface 190 can include a series of buttons, a pointing device, or another input mechanism for operator entry of data.

Molecular reader 100 further includes a communications interface 180 in electrical communication with electronic processor 170. Communications interface 180 is configured to transmit signals from electronic processor 170 to devices external to reader 100, and to receive signals from external devices and transmit the received signals to electronic processor 170. In some embodiments, for example, communications interface 180 can include a wireless communications interface (e.g., a wireless signal transmitter and receiver). In certain embodiments, communications interface 180 can include an interface for transmitting and/or receiving signals over conventional electrical wires.

In some embodiments, communications interface 180 can be configured to transmit data to, and/or receive data from, an external device via a direct connection to the device. In certain embodiments, communications interface 180 can be configured to transmit data to, and/or receive data from, an external device over a network such as a cellular telephone network, a radio network, or a computer network such as a local area network, a wide area network, or the internet.

7. Device Housing

Figure 10:
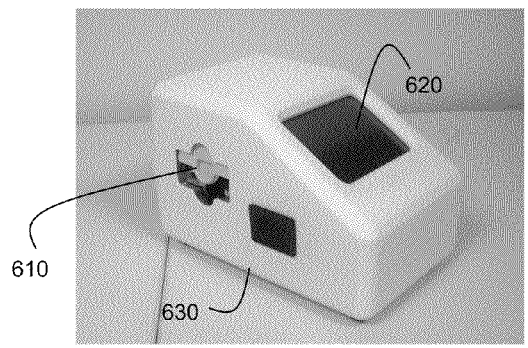
FIG. 10 is a schematic diagram showing an embodiment of a molecular reader.
Figure 11:
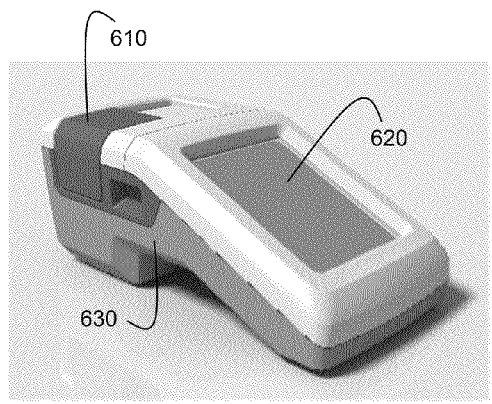
FIG. 11 is a schematic diagram showing another embodiment of a molecular reader.

FIGS. 10 and 11 show two different embodiments of molecular reader 100, each with a different external housing 110. Each of the embodiments shown in FIGS. 10 and 11 includes a door 610 that opens to admit chip 130, and a display screen 620 integrated within the housing. Display screen 620 is in electrical communication with electronic processor 170, as discussed above.

In some embodiments, molecular reader 100 includes a barcode reader 630 integrated into housing 110. Barcode reader 630 is in electrical communication with processor 170. Chips 130 can include a barcode featuring the chip's part number, lot number, and/or serial number; this information can be read by barcode reader 630. In certain embodiments, barcode reader 630 can distinguish between read barcodes that correspond to different samples and/or patient records. Prior to inserting a particular chip into reader 100, the chip's barcode can be scanned via barcode reader 630. In certain embodiments, barcode reader 630 can also read barcodes that correspond to different samples and/or patient records. Then, the chip can be inserted into reader 100 and one or more analysis protocols can be executed. The results of the analysis can be tagged with the identity of the sample as determined from the sample barcode and the identity of the chip 130 from the chip barcode, and the tagged results can be stored onboard reader 100 and/or transmitted to an external device by processor 170. In certain embodiments, instead of being integrated into housing 110 of reader 100, barcode reader 630 can be positioned internally in reader 100. The barcode reader can read the barcode of chip 130 automatically following insertion of chip 130 into reader 100.

Typically, samples are introduced into chip 130 before chip 130 is inserted into molecular reader 100. In certain embodiments, however, samples can be introduced after chip 130 has been inserted. For example, external housing 110 can include an injection port that permits access to chip 130 in its mounted position on stage 120 within reader 100. After chip 130 has been mounted, samples can be introduced into chip 130 via the injection port, just prior to initiating an analysis protocol. This feature can be particularly useful for analytes that are sensitive to their environment and, consequently, cannot be stored for long periods of time or manipulated extensively.

Generally, molecular reader 100 is a compact, portable device that can be transported relatively easily from one location to another. In some embodiments, for example, a maximum dimension of reader 100 is less than 10 inches (e.g., less than 9 inches, less than 8 inches, less than 7 inches, less than 6 inches, less than 5 inches, less than 4 inches). In certain embodiments, a total mass of reader 100 is 10 pounds or less (e.g., 9 pounds or less, 8 pounds or less, 7 pounds or less, 6 pounds or less, 5 pounds or less).

III. Chip Technology

Molecular reader 100 can function with a wide variety of different microfluidic chips 130 to perform measurements of analytes positioned within the chips. To operate with various different chip designs, reader 100 performs various different functions, some or all of which may be part of a particular measurement protocol. Functions and operating modes provided by reader 100 include, but are not limited to:

(i) Fluid Propulsion:

Chip 130 typically includes a plurality of channels in fluid communication with one another, and an outlet to which an air-tight connection can be made. Reader 100 is capable of automatically and reversibly establishing an air-tight connection between the outlet and a pump and/or a vacuum source, and applying positive or negative fluid (e.g., air) pressure to the plurality of channels.

(ii) Fluid Flow Control:

At least a portion of the plurality of channels in chip 130 can be formed from a layer of a deformable material, and a layer of a more rigid material that exposes at least a portion of the deformable material layer. The channels in chip 130 are sized such that they can be completely closed off by the application of pressure to the deformable material layer, which causes the walls of the channels to be deformed and the interior region of the channels enclosed by the walls to be reduced in cross-sectional area. Reader 100 is configured to apply pressure in a controlled and reproducible manner to the layer of deformable material, reducing the cross-sectional area of certain channels (and even closing off certain channels), thereby controlling fluid flow within the channels of chip 130.

(iii) Controlled Heating of the Chip:

Chip 130 can include one or more embedded thermal elements 131. Thermal element 131 can be, for example, a relatively inexpensive thermistor, or another element with an electrical resistance that varies according to temperature. As discussed previously, thermal control module 135 in reader 100 can connect to thermal element 131 to monitor the temperature of chip 130 and/or to heat chip 130. Reader 100 is configured to automatically and reversibly make electrical contact with thermal element 131. When contact is established, reader 100 can heat chip 130 (e.g., resistively) by applying an electrical potential across the terminals of thermal element 131. Alternatively, or in addition, reader 100 can measure a temperature of chip 130 by measuring an electrical resistance of thermal element 131. The measured resistance can be converted into a temperature measurement by referring to a lookup table and/or by calculating the temperature from the resistance, for example. In some embodiments, the measured resistance and/or temperature can be used for feedback control of a heating circuit and/or algorithm implemented in reader that performs controlled heating of chip 130.

(iv) Multiplex Capture of Multiple Analytes:

Chip 130 can include an array of immobilized capture sites over which the sample, which can include multiple analytes, can be directed by reader 100 to flow. Analytes present in the sample can bind to the capture sites. Reader 100 can perform two-dimensional optical imaging of the array of capture sites; a field of view and a resolution of the optical sub-system of reader 100 can be selected according to the size of the capture sites and to the overall array. Furthermore, reader 100 can position chip 130, either actively or passively, so that high-quality images of an area of interest within the array can be acquired.

(v) Analyte Detection:

Chip 130 permits optical detection of bound analytes with or without the addition of chemical reagents and/or tags to capture sites. Reader 100 is directing radiation to be incident on the array. The incident radiation induces a response (e.g., fluorescence emission) by the bound analytes. The response is detected by a detector and converted to an electronic signal in reader 100. The magnitude of the signal can be correlated with the amount of bound analyte(s) in the array, permitting quantification of the analyte(s) in the original sample.

(vi) Sample and Chip Tracking:

Chip 130 can include a bar code which can identify the configuration of the chip, the configuration of the capture array, and can provide other information such as information about the sample contained in the chip. Reader 100 can include a bar code reader for reading this information; measurement results can be correlated, stored, and/or reported together with information scanned from the bar code.

Molecular reader 100 is compatible with a wide variety of different types of microfluidic chips. Exemplary chips and/or chip features are disclosed, for example, in: U.S. patent application Ser. No. 11/875,031, now published as U.S. Patent Application Publication No. US 2009/0032399; and Wang, J. et al., "Microfluidic Cell Electroporation Using a Mechanical Valve," *Analytical Chemistry* 79: 9584-9587 (2007).

Figure 12:
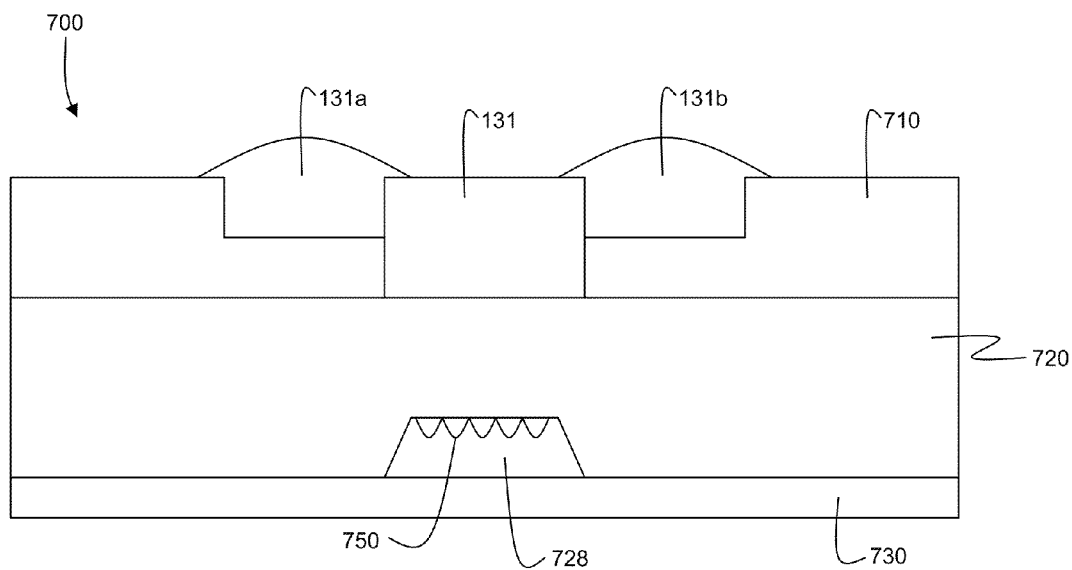
FIG. 12 is a schematic cross-sectional diagram of a microfluidic chip.

FIG. 12 shows a schematic diagram of an exemplary chip 700. Chip 700 includes an analysis region 728 that includes an array of capture sites to bind analyte molecules. Analysis region 728 includes a plurality of binding sites 750 for analytes of interest and is formed in a channel plate 720. Thermal element 131 is positioned in a top plate 710 (e.g., in an aperture of top plate 710). Electrical contacts 131a and 131b of thermal element 131 are contacted by contact pins 136 of reader 100 during use. Typically, for example, electrical contacts 131a and 131b are formed of a material such as conductive epoxy.

Microfluidic chips used in connection with molecular reader 100 are typically formed from multiple layers of materials. Top plate 710 can be formed of a plastic material for example. Channel plate 720 can be formed of a deformable material. A substrate 730 can be positioned, for example, in contact with a lower surface of channel plate 720 to enclose channels formed in channel plate 720. Substrate 730 can be formed of a material having a high optical quality, such as glass.

In some embodiments, thermal element 131 can be, for example, a thermistor, or another element with an electrical resistance that varies according to temperature. As discussed previously, thermal control module in reader 100 can connect to thermal element 131 to monitor the temperature of chip 700 and/or to heat chip 700.

Actuators 142 contact channel plate 720 through apertures formed in top plate 710 (not shown in FIG. 12). A plurality of channels are formed in channel plate 720 for conveying fluids from one region of plate 720 to another. By applying pressure to the walls of the channels formed in channel plate 720, actuators 142 can control the cross-sectional area of the channels, thereby regulating fluid flow through the channels.

Channel plate 720 is formed of a deformable material. Typically, for example, channel plate 720 is molded from an elastomeric polymer material such as PDMS, PDMA, or PMMA. More generally, a wide variety of different materials, including polymer materials and plastic materials, can be used to form channel plate 720.

In some embodiments, either or both of top plate 710 and substrate 730 can be formed from one material or from multiple materials. The materials selected for top plate 710 and/or substrate 730 can be transmissive at particular wavelengths within the electromagnetic spectrum. In particular, top plate 710 and/or substrate 730 can transmit about 50% or more (e.g., about 60% or more, about 70% or more, about 80% or more, about 90% or more, about 95% or more, about 99% or more) of incident light generated by light source 150, and/or about 50% or more (e.g., about 60% or more, about 70% or more, about 80% or more, about 90% or more, about 95% or more, about 99% or more) of emitted light from the sample within chip 700. Materials that can be used to form top plate 710 and/or substrate 730 can include, for example, polymers, glasses, quartz, fused silica, sapphire, and various plastics.

Channel plate 720 includes a plurality of channels. The channels can be formed using a variety of processes, depending upon the material of channel plate 720. Exemplary processes include molding, etching (e.g., UV, x-ray, plasma or chemical etching), and photolithography. Channel plate 720 can also include one or more waste reservoirs, one or more reservoirs for buffer solutions, one or more sample reservoirs, and one or more reservoirs for additional chemical agents such as solutions of tagging agents, washing solutions, water, and other substances that are used in the sample's analysis protocol.

IV. Computer Hardware and Software

The steps described above in connection with various methods for collecting, processing, analyzing, interpreting, and displaying information from samples can be implemented in computer programs using standard programming techniques. Such programs are designed to execute on programmable computers or specifically designed integrated circuits, each comprising an electronic processor (e.g., electronic processor 170), a data storage system (including memory and/or storage elements), at least one input device, and least one output device, such as a display or printer.

Data analysis functions performed by the reader's software can include shape detection of a bright field image to determine, for example, approximately circular image features corresponding to capture areas in a microarray, to determine image features corresponding to fluorescing areas in a completed assay, and to locate fiducial marks positioned on the chip. The reader can also locate each of the detected image features relative to reference features such as the edges of a CCD sensor area. In some embodiments, the molecular reader can label particular imaged areas with an index corresponding to a particular type of analyte or binding agent. The reader can be configured to measure to determine fluorescence intensity at each bead position in an array, for example, by selecting a particular subset of image pixels corresponding to each area, and then adding the measured light intensities of each of the selected pixels. The fluorescence intensity for each area can be correlated with values of measured intensity as a function of analyte (e.g., protein) concentration derived, for example, from a calibration curve, to determine the concentration of the analyte in the sample of interest. In some embodiments, the molecular readers disclosed herein can be configured to compare measured concentrations of multiple analytes in a sample to interest to reference data (e.g., reference tables of data and/or an expert systems-derived algorithm) to provide a disease diagnosis, a water quality assessment, or another type of estimation, judgment, or determination regarding the quality, condition, or state of the sample of interest. Each of the foregoing functions can be implemented in molecular reader 100 in software, in hardware, or in a combination of hardware and software.

The program code is applied to input data to perform the functions described herein and generate output information which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis and control functions described herein.

V. Applications

In the preceding discussion, molecular reader 100 has been applied to the detection and quantification of a variety of biological molecules and structures, including amino acid-based molecules such as protein, and nucleic acid-based molecules such as DNA and RNA. More generally, molecular reader 100 can also be used to detect and quantify other types of biological chemical species, including chemical weapons, explosives, and environmental pollutants. Molecular reader 100 can be implemented as a stand-alone devices, or as part of a larger instrument such as a laboratory microscope. Further, molecular reader 100 can implement particular analysis protocols according to the instructions of a system operator; for example, reader 100 can be configured to perform immunoassays to detect various types of chemical and biological agents.

Exemplary applications of reader 100 include performing assays to detect any one or more of the following different types of compounds: petroleum compounds, see for example U.S. Pat. No. 5,015,586; chemical nerve agents, see for example Bencic-Nagale, S. et al., "Microbead Chemical Switches: An Approach to Detection of Reactive Organophosphate Chemical Warfare Agent Vapors," J. *Am. Chem. Soc.* 128: 5041-5048 (2006); polychlorinated biphenyls, see for example U.S. Pat. Nos. 5,834,222 and 5,858,692; pesticides, see for example U.S. Pat. Nos. 5,981,196, 5, 981,298, and 6,635,434; herbicides, see for example U.S. Pat. No. 4,780,408; and water treatment polymers, see for example U.S. Pat. No. 6,420,530. The entire contents of all of the foregoing publications and U.S. patents are incorporated by reference herein.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. A system, comprising:
a support apparatus configured to detachably receive a chip;
a plurality of movable pins extendible from a first position to a second position, wherein:
in the first position, the movable pins do not contact the chip when the chip is positioned on the support apparatus; and
in the second position, the movable pins contact electrical terminals of a heating element within the chip when the chip is positioned on the support apparatus;
a radiation source configured to direct radiation to be incident on the chip when the chip is positioned on the support apparatus;
a detector configured to detect radiation emitted from the chip when the chip is positioned on the support apparatus; and
an electronic processor in electrical communication with the plurality of movable pins and the detector, wherein the electronic processor is configured to detect molecules in a sample positioned within the chip by analyzing the detected radiation, and to determine a temperature of the chip by measuring an electrical resistance between two of the multiple pins connected to the electrical terminals.

2. The system of claim 1, wherein the electronic processor is configured to cause at least some of the plurality of movable pins to extend from the first position to the second position when the chip is received by the support apparatus.

3. The system of claim 1, wherein the electronic processor is configured to control the temperature of a localized area of the chip by applying an electrical potential difference between the electrical terminals.

4. The system of claim 1, further comprising a movable vacuum source extendible from a first vacuum position not in contact with the chip to a second vacuum position in contact with the chip when the chip is positioned on the support apparatus.

5. The system of claim 4, wherein the electronic processor is configured to extend the vacuum source from the first vacuum position to the second vacuum position to form a fluid connection with a channel positioned in the chip.

6. The system of claim 1, further comprising at least one extendible member electrically connected to the electronic processor and positioned so that when the chip is received by the support apparatus, the at least one extendible member contacts the chip and extends to deform a wall of a channel formed within the chip.

7. The system of claim 6, wherein the electronic processor controls movement of the at least one extendible member between a first position where the at least one extendible member applies a first pressure to the channel wall, and a second position where the at least one extendible member applies a second pressure different from the first pressure to the channel wall, and wherein the electronic processor controls an open cross-sectional area of the channel by controlling the extension of the at least one extendible member.

8. The system of claim 1, wherein the detector is configured to acquire an image of the chip when the chip is received by the support apparatus, and wherein the electronic processor is configured to determine the position of the chip and whether the chip is positioned correctly based on the image.

9. The system of claim 1, further comprising a housing that encloses the support apparatus, the plurality of movable pins, the radiation source, the detector, and the electronic processor, the housing having an opening through which the chip can be received by the support apparatus, and a closing member adjustable between an open position wherein the opening is at least partially unobstructed by the closing member and a closed position wherein the closing member seals the opening.

10. The system of claim 9, wherein the closing member is mechanically coupled to at least some of the plurality of movable pins so that when the closing member is moved from the open position to the closed position, the at least some of the plurality of movable pins are moved from the first position to the second position.

11. The system of claim 1, wherein the electronic processor is configured to detect at least one of molecules comprising amino acids and molecules comprising nucleic acids in a sample positioned within the chip.

12. The system of claim 1, further comprising a communications interface, wherein the electronic processor is configured to transmit data to, and receive data from, one or more external devices through the communications interface.

13. The system of claim 12, wherein the communications interface comprises a wireless transmitter and receiver electrically coupled to the electronic processor and configured to transmit and receive electronic signals.

14. A system, comprising:
a support apparatus configured to detachably receive a chip;
at least one extendible member positioned so that when the chip is received by the support apparatus, the at least one extendible member contacts the chip in a first member position and extends to deform a wall of a channel formed within the chip in a second member position;
a radiation source configured to direct radiation to be incident on the chip when the chip is positioned on the support apparatus;
a detector configured to detect radiation emitted from the chip when the chip is positioned on the support apparatus; and
an electronic processor in electrical communication with the at least one extendible member and the detector,
wherein the electronic processor is configured to detect molecules in a sample positioned within the chip by analyzing the detected radiation; and
wherein the electronic processor is configured to regulate a flow of fluid through the channel by controlling an extension of the at least one extendible member.

15. The system of claim 14, further comprising a plurality of movable pins extendible from a first position to a second position, wherein:
in the first position, the movable pins do not contact the chip when the chip is positioned on the support apparatus; and
in the second position, the movable pins contact electrical terminals of a heating element within the chip when the chip is positioned on the support apparatus; and
wherein the electronic processor is in electrical communication with the plurality of movable pins.

16. The system of claim 15, wherein the electronic processor is configured to cause at least some of the plurality of movable pins to extend from the first position to the second position when the chip is received by the support apparatus.

17. The system of claim 15, further comprising:
a housing that encloses the support apparatus, the plurality of movable pins, the at least one extendible member, the radiation source, the detector, and the electronic processor, the housing having an opening through which the chip can be received by the support apparatus, and a closing member adjustable between an open position wherein the opening is at least partially unobstructed by the closing member and a closed position wherein the closing member seals the opening, and
wherein the closing member is mechanically coupled to at least some of the plurality of movable pins so that when the closing member is moved from the open position to the closed position, the at least some of the plurality of movable pins are moved from the first position to the second position.

18. The system of claim 14, further comprising a movable vacuum source extendible from a first vacuum position not in contact with the chip to a second vacuum position in contact with the chip when the chip is positioned on the support apparatus, and wherein the electronic processor is configured to extend the vacuum source from the first vacuum position to the second vacuum position to form a fluid connection with a vacuum channel positioned in the chip.

19. The system of claim 14, wherein the at least one extendible member comprises a motorized actuator coupled to the electronic processor.

20. The system of claim 19, wherein the motorized actuator comprises a shaft coupled to a rotatable disc comprising at least one pin, and wherein the at least one pin deforms the wall of the channel.

21. The system of claim 19, wherein the motorized actuator comprises at least one pin coupled to a spring, and the actuator further comprises a rotating camshaft that controls an extension of the at least one pin.

22. The system of claim 14, wherein the electronic processor controls movement of the at least one extendible member between the first member position where the at least one extendible member applies a first pressure to the channel wall, and the second member position where the at least one extendible member applies a second pressure different from the first pressure to the channel wall.

23. The system of claim 14, further comprising a housing that encloses the support apparatus, the at least one extendible member, the radiation source, the detector, and the electronic processor, the housing having an opening through which the chip can be received by the support apparatus, and a closing member adjustable between an open position wherein the opening is at least partially unobstructed by the closing member and a closed position wherein the closing member seals the opening.

24. A method, comprising:
positioning a chip on a support stage configured to detachably receive the chip; extending a plurality of movable pins from a first position not in contact with the chip to a second position wherein the movable pins contact electrical terminals of a heating element within the chip;
directing illumination radiation to be incident on the chip;
measuring radiation emitted from the chip; and
detecting molecules in a sample positioned within the chip based on the measured radiation.

25. The method of claim 24, further comprising one of measuring a temperature of the chip and controlling a temperature of the chip by applying an electrical potential difference between the electrical terminals.

26. The method of claim 24, further comprising positioning a vacuum source into fluid communication with a vacuum channel formed in the chip.

27. The method of claim 24, further comprising, prior to extending the plurality of movable pins, measuring an image of the chip on the support stage and determining a position of the chip relative to the stage based on the image.

28. A method, comprising:
positioning a chip on a support stage configured to detachably receive the chip;
positioning an extendible member at a first member position so that the member contacts a wall of a channel formed in the chip;

regulating a flow of fluid through the channel by extending the extendible member to a second member position to control a cross-sectional shape of the channel;
directing illumination radiation to be incident on the chip;
measuring radiation emitted from the chip; and
detecting molecules in a sample positioned within the chip based on the measured radiation.

29. The method of claim 28, further comprising extending a plurality of movable pins from a first position not in contact with the chip to a second position wherein the movable pins contact electrical terminals of a heating element within the chip.

30. The method of claim 29, further comprising at least one of measuring a temperature of the chip and controlling a temperature of the chip by applying an electrical potential difference between the electrical terminals.

31. The method of claim 28, further comprising positioning a vacuum source into fluid communication with a vacuum channel formed in the chip.

32. The method of claim 28, further comprising, prior to positioning the extendible member, measuring an image of the chip on the support stage and determining a position of the chip relative to the stage based on the image.

33. The method of claim 28, wherein the molecules in the sample are detected based on a measurement of emitted radiation at one central wavelength.

34. The method of claim 28, wherein detecting molecules in the sample comprises detecting both molecules comprising amino acids and molecules comprising nucleic acids in the sample.

* * * * *